US012778797B2

(12) United States Patent
Daw et al.

(10) Patent No.: US 12,778,797 B2
(45) Date of Patent: Nov. 3, 2026

(54) SOFT BORDER FOR TARGETED TEMPERATURE MANAGEMENT

(71) Applicant: C. R. Bard, Inc., Franklin Lakes, NJ (US)

(72) Inventors: Kyle Daw, Smyrna, GA (US); Jill D. Tabaka, Rochester, MN (US); Mary Bolen, Oxford, GA (US); Sean E. Walker, Platteville, CO (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 352 days.

(21) Appl. No.: 18/274,436

(22) PCT Filed: Jan. 27, 2022

(86) PCT No.: PCT/US2022/014147
§ 371 (c)(1),
(2) Date: Jul. 26, 2023

(87) PCT Pub. No.: WO2022/165068
PCT Pub. Date: Aug. 4, 2022

(65) Prior Publication Data

US 2024/0108497 A1 Apr. 4, 2024

Related U.S. Application Data

(60) Provisional application No. 63/142,397, filed on Jan. 27, 2021.

(51) Int. Cl.
*A61F 7/02* (2006.01)
*A61F 7/00* (2006.01)

(52) U.S. Cl.
CPC ........ *A61F 7/02* (2013.01); *A61F 2007/0054* (2013.01); *A61F 2007/0226* (2013.01);
(Continued)

(58) Field of Classification Search
CPC ............................................. A61F 2007/0054
See application file for complete search history.

(56) References Cited

U.S. PATENT DOCUMENTS 2,167,865 A 8/1939 Beecher
2,250,325 A 7/1941 Barnes
(Continued)

FOREIGN PATENT DOCUMENTS

AU 678753 B3 6/1997
AU 2007201161 B2 12/2010
(Continued)

OTHER PUBLICATIONS

PCT/US2021/065144 filed Dec. 23, 2021 International Search Report dated Oct. 4, 2022.
(Continued)

*Primary Examiner* — Kaitlyn E Smith
(74) *Attorney, Agent, or Firm* — Rutan & Tucker LLP

(57) ABSTRACT

Disclosed herein is an apparatus and system directed to providing for a patients comfort while undergoing Targeted Temperature Management (TTM). A medical pad with the TTM can include a flexible upper sheet, a flexible base member, an adhesive surface, and an edge guard. The flexible base member can be interconnected to the flexible upper sheet to define a fluid containing layer including a plurality of tortuous fluid flow paths. The adhesive surface can be disposed on a skin-contacting side of the flexible upper sheet, and can be adapted for releasable adhesive contact with skin of the patient. The edge guard can include a pliant shock-absorbent material surrounding a portion of an edge of the flexible upper sheet, and can be configured to distribute pressure from the medical pad across a portion of the patients body in contact with a surface of the edge guard.

30 Claims, 10 Drawing Sheets

(52) U.S. Cl.
CPC ................. *A61F 2007/0247* (2013.01); *A61F 2007/0277* (2013.01)

(56) References Cited

U.S. PATENT DOCUMENTS

| | | | |
|---|---|---|---|
| 2,296,207 A | 9/1942 | Joyce | |
| 2,595,328 A | 5/1952 | Bowen | |
| 2,602,302 A | 7/1952 | Poux | |
| 2,726,658 A | 12/1955 | Chessey | |
| 2,807,809 A | 10/1957 | Kottemann | |
| 3,075,529 A | 1/1963 | Young, Jr. | |
| 3,091,242 A | 5/1963 | Johnson et al. | |
| 3,212,286 A | 10/1965 | Curtis | |
| 3,506,013 A | 4/1970 | Zdenek | |
| 3,734,293 A | 5/1973 | Biskis | |
| 3,830,676 A | 8/1974 | Elkins | |
| 3,867,939 A | 2/1975 | Moore et al. | |
| 3,900,035 A | 8/1975 | Welch et al. | |
| 3,927,671 A | 12/1975 | Chittenden et al. | |
| 3,945,617 A | 3/1976 | Callery | |
| 3,995,621 A | 12/1976 | Fletcher et al. | |
| 4,059,293 A | 11/1977 | Sipler | |
| 4,092,982 A | 6/1978 | Salem | |
| 4,108,146 A | 8/1978 | Golden | |
| 4,114,620 A | 9/1978 | Moore et al. | |
| 4,118,946 A | 10/1978 | Tubin | |
| 4,149,541 A | 4/1979 | Gammons et al. | |
| 4,154,245 A | 5/1979 | Daily | |
| 4,161,210 A | 7/1979 | Reid et al. | |
| 4,195,631 A | 4/1980 | Baucom | |
| 4,311,022 A | 1/1982 | Hall | |
| 4,444,727 A | 4/1984 | Yanagihara et al. | |
| 4,508,123 A | 4/1985 | Wyatt et al. | |
| 4,580,408 A | 4/1986 | Stuebner | |
| 4,753,241 A | 6/1988 | Brannigan et al. | |
| 4,834,705 A | 5/1989 | Vaillancourt | |
| 4,846,176 A | 7/1989 | Golden | |
| 4,867,748 A | 9/1989 | Samuelsen | |
| 4,884,304 A | 12/1989 | Elkins | |
| 4,886,063 A | 12/1989 | Crews | |
| 4,908,248 A | 3/1990 | Nakashima et al. | |
| 4,919,134 A | 4/1990 | Streeter | |
| 4,962,761 A | 10/1990 | Golden | |
| 4,971,056 A | 11/1990 | Seacord | |
| 4,981,135 A | 1/1991 | Hardy | |
| 4,989,607 A | 2/1991 | Keusch et al. | |
| 5,000,252 A | 3/1991 | Faghri | |
| 5,005,374 A | 4/1991 | Spitler | |
| 5,050,596 A | 9/1991 | Walasek et al. | |
| 5,062,414 A | 11/1991 | Grim | |
| 5,072,875 A | 12/1991 | Zacoi | |
| 5,090,409 A | 2/1992 | Genis | |
| 5,097,829 A | 3/1992 | Quisenberry | |
| 5,111,668 A | 5/1992 | Parrish et al. | |
| 5,113,666 A | 5/1992 | Parrish et al. | |
| 5,133,348 A | 7/1992 | Mayn | |
| 5,146,625 A | 9/1992 | Steele et al. | |
| 5,154,706 A | 10/1992 | Cartmell et al. | |
| 5,190,032 A | 3/1993 | Zacoi | |
| 5,265,669 A | 11/1993 | Schneider | |
| 5,268,022 A | 12/1993 | Garrett et al. | |
| 5,289,695 A | 3/1994 | Parrish et al. | |
| 5,300,103 A | 4/1994 | Stempel et al. | |
| 5,304,213 A | 4/1994 | Berke et al. | |
| 5,304,216 A | 4/1994 | Wallace | |
| 5,320,164 A | 6/1994 | Szczesuil et al. | |
| 5,329,638 A * | 7/1994 | Hansen | A41D 13/088 2/16 |
| 5,383,919 A | 1/1995 | Kelly et al. | |
| 5,393,462 A | 2/1995 | Avery | |
| 5,405,366 A | 4/1995 | Fox et al. | |
| 5,407,421 A | 4/1995 | Goldsmith | |
| 5,409,500 A | 4/1995 | Dyrek | |
| 5,411,541 A | 5/1995 | Bell et al. | |
| 5,423,751 A | 6/1995 | Harrison et al. | |
| 5,431,622 A | 7/1995 | Pyrozyk et al. | |
| 5,437,673 A | 8/1995 | Baust et al. | |
| 5,456,701 A | 10/1995 | Stout | |
| 5,466,250 A | 11/1995 | Johnson, Jr. et al. | |
| 5,470,353 A | 11/1995 | Jensen | |
| 5,476,489 A | 12/1995 | Koewler | |
| 5,484,448 A | 1/1996 | Steele et al. | |
| 5,486,207 A | 1/1996 | Mahawili | |
| 5,514,169 A | 5/1996 | Dickerhoff et al. | |
| 5,545,194 A | 8/1996 | Augustine | |
| 5,566,413 A | 10/1996 | Webb et al. | |
| 5,605,144 A | 2/1997 | Simmons et al. | |
| 5,609,620 A | 3/1997 | Daily | |
| 5,620,482 A | 4/1997 | Augustine et al. | |
| 5,624,477 A | 4/1997 | Armond | |
| 5,634,940 A | 6/1997 | Panyard | |
| 5,640,728 A | 6/1997 | Graebe | |
| 5,645,855 A | 7/1997 | Lorenz | |
| 5,658,325 A | 8/1997 | Augustine | |
| 5,662,695 A | 9/1997 | Mason et al. | |
| 5,683,439 A | 11/1997 | Jensen | |
| 5,720,774 A | 2/1998 | Glucksman | |
| 5,733,318 A | 3/1998 | Augustine | |
| 5,755,755 A | 5/1998 | Panyard | |
| 5,785,716 A | 7/1998 | Bayron et al. | |
| 5,806,335 A | 9/1998 | Herbert et al. | |
| 5,824,025 A | 10/1998 | Augustine | |
| 5,837,002 A | 11/1998 | Augustine et al. | |
| 5,840,080 A | 11/1998 | Der Ovanesian | |
| 5,843,145 A | 12/1998 | Brink | |
| 5,871,526 A | 2/1999 | Gibbs et al. | |
| 5,879,378 A | 3/1999 | Usui | |
| 5,887,437 A | 3/1999 | Maxim | |
| 5,913,849 A | 6/1999 | Sundstrom et al. | |
| 5,947,914 A | 9/1999 | Augustine | |
| 5,948,012 A | 9/1999 | Mahaffey et al. | |
| 5,968,000 A | 10/1999 | Harrison et al. | |
| 5,986,163 A | 11/1999 | Augustine | |
| 5,989,285 A | 11/1999 | DeVilbiss et al. | |
| 6,010,528 A | 1/2000 | Augustine et al. | |
| 6,019,783 A | 2/2000 | Philips et al. | |
| 6,030,412 A | 2/2000 | Klatz et al. | |
| 6,047,106 A | 4/2000 | Salyer | |
| 6,074,415 A | 6/2000 | Der Ovanesian | |
| 6,083,256 A | 7/2000 | Der Ovanesian | |
| 6,083,418 A | 7/2000 | Czarnecki et al. | |
| 6,117,164 A | 9/2000 | Gildersleeve et al. | |
| 6,176,869 B1 | 1/2001 | Mason et al. | |
| 6,176,870 B1 | 1/2001 | Augustine | |
| 6,185,744 B1 | 2/2001 | Poholski | |
| 6,188,930 B1 | 2/2001 | Carson | |
| 6,189,149 B1 | 2/2001 | Allen | |
| 6,189,550 B1 | 2/2001 | Stickel et al. | |
| 6,197,045 B1 | 3/2001 | Carson | |
| 6,234,538 B1 | 5/2001 | Lauer | |
| 6,238,427 B1 | 5/2001 | Matta | |
| 6,255,552 B1 | 7/2001 | Cummings et al. | |
| 6,257,011 B1 | 7/2001 | Siman-Tov et al. | |
| 6,290,716 B1 | 9/2001 | Augustine | |
| 6,336,935 B1 | 1/2002 | Davis et al. | |
| 6,349,560 B1 | 2/2002 | Maier-Laxhuber et al. | |
| 6,352,550 B1 * | 3/2002 | Gildersleeve | A61F 7/02 607/108 |
| 6,364,937 B1 | 4/2002 | McMahon | |
| 6,371,976 B1 | 4/2002 | Vrzalik et al. | |
| 6,375,674 B1 | 4/2002 | Carson | |
| 6,389,839 B1 | 5/2002 | Sabin | |
| 6,436,130 B1 | 8/2002 | Philips et al. | |
| 6,451,036 B1 | 9/2002 | Heitzmann et al. | |
| 6,454,792 B1 | 9/2002 | Noda et al. | |
| 6,461,379 B1 | 10/2002 | Carson et al. | |
| 6,463,212 B1 | 10/2002 | Salyer | |
| 6,503,297 B1 | 1/2003 | Lu et al. | |
| 6,508,831 B1 | 1/2003 | Kushnir | |
| 6,508,859 B1 | 1/2003 | Zia et al. | |
| 6,511,501 B1 | 1/2003 | Augustine et al. | |
| 6,511,502 B2 | 1/2003 | Fletcher | |
| 6,517,510 B1 | 2/2003 | Stewart et al. | |
| D471,987 S | 3/2003 | Hoglund et al. | |

(56) References Cited

U.S. PATENT DOCUMENTS

D472,322 S 3/2003 Hoglund et al.
6,551,348 B1 4/2003 Blalock et al.
D474,544 S 5/2003 Hoglund et al.
6,559,096 B1 5/2003 Smith et al.
6,584,797 B1 7/2003 Smith et al.
6,589,270 B2 7/2003 Augustine
6,591,630 B2 7/2003 Smith et al.
6,601,404 B1 8/2003 Roderick
6,613,030 B1 9/2003 Coles et al.
6,620,187 B2 9/2003 Carson et al.
6,620,188 B1 9/2003 Ginsburg et al.
6,645,232 B2 11/2003 Carson
6,648,905 B2 11/2003 Hoglund et al.
6,653,607 B2 11/2003 Ellis et al.
D483,125 S 12/2003 Hoglund et al.
6,660,027 B2 12/2003 Gruszecki et al.
6,669,715 B2 12/2003 Hoglund et al.
6,682,525 B2 1/2004 Lalonde et al.
D487,147 S 2/2004 Ellingboe et al.
D487,148 S 2/2004 Ellingboe et al.
6,688,132 B2 2/2004 Smith et al.
6,692,518 B2 2/2004 Carson
6,699,267 B2 3/2004 Voorhees et al.
6,701,724 B2 3/2004 Smith et al.
6,743,250 B2 6/2004 Renfro
6,755,801 B2 6/2004 Utterberg et al.
6,755,852 B2 6/2004 Lachenbruch et al.
D492,773 S 7/2004 Ellingboe et al.
6,770,848 B2 8/2004 Haas et al.
6,799,063 B2 9/2004 Carson
6,800,087 B2 10/2004 Papay et al.
6,802,855 B2 10/2004 Ellingboe et al.
6,802,885 B2 10/2004 Luk et al.
6,818,012 B2 11/2004 Ellingboe
6,827,728 B2 12/2004 Ellingboe et al.
6,846,322 B2 1/2005 Kane et al.
6,858,068 B2 2/2005 Smith et al.
6,878,156 B1 4/2005 Noda
6,893,453 B2 5/2005 Agarwal et al.
6,904,956 B2 6/2005 Noel
6,909,074 B1 6/2005 Bradley
6,921,198 B2 7/2005 Gruszecki et al.
6,931,875 B1 8/2005 Allen et al.
6,942,644 B2 9/2005 Worthen
6,960,243 B1 11/2005 Smith et al.
6,968,711 B2 11/2005 Smith et al.
6,969,399 B2 11/2005 Schock et al.
7,008,445 B2 3/2006 Lennox
7,022,099 B2 4/2006 Litzie et al.
7,044,960 B2 5/2006 Voorhees et al.
7,052,509 B2 5/2006 Lennox et al.
7,055,575 B2 6/2006 Noel
7,056,335 B2 6/2006 Agarwal et al.
7,063,718 B2 6/2006 Dobak, III
7,077,858 B2 7/2006 Fletcher et al.
7,097,657 B2 8/2006 Noda et al.
7,101,389 B1 9/2006 Augustine et al.
7,122,047 B2 10/2006 Grahn et al.
7,160,316 B2 1/2007 Hamilton et al.
7,172,586 B1 2/2007 Dae et al.
7,240,720 B2 7/2007 Noel
7,303,554 B2 12/2007 Lalonde et al.
7,303,579 B2 12/2007 Schock et al.
7,338,516 B2 3/2008 Quincy, III et al.
7,361,186 B2 4/2008 Voorhees et al.
7,377,935 B2 5/2008 Schock et al.
7,507,250 B2 3/2009 Lennox
7,517,360 B2 4/2009 Frey et al.
RE40,815 E 6/2009 Kudaravalli et al.
7,547,320 B2 6/2009 Schook et al.
RE40,868 E 8/2009 Ryba et al.
7,621,944 B2 11/2009 Wilson et al.
7,621,945 B2 11/2009 Lennox et al.
7,666,213 B2 2/2010 Freedman, Jr. et al.
7,678,716 B2 3/2010 Yahiaoui et al.
7,686,840 B2 3/2010 Quincy, III et al.
7,727,228 B2 6/2010 Abboud et al.
7,731,739 B2 6/2010 Schock et al.
7,744,640 B1 6/2010 Faries, Jr. et al.
7,749,261 B2 7/2010 Hansen et al.
7,763,061 B2 7/2010 Schorr et al.
7,771,461 B2 8/2010 Schock et al.
7,784,304 B2 8/2010 Trinh et al.
7,799,063 B2 9/2010 Ingram et al.
7,827,815 B2 11/2010 Carson et al.
7,867,266 B2 1/2011 Collins
7,892,269 B2 2/2011 Collins et al.
7,896,910 B2 3/2011 Schirrmacher et al.
7,918,243 B2 4/2011 Diodati et al.
8,047,010 B2 11/2011 Carson et al.
8,052,624 B2 11/2011 Buchanan et al.
8,066,752 B2 11/2011 Hamilton et al.
8,182,521 B2 5/2012 Kane et al.
8,187,697 B2 5/2012 Quincy, III et al.
8,216,163 B2 7/2012 Edelman
8,283,602 B2 10/2012 Augustine et al.
8,454,671 B2 6/2013 Lennox et al.
D685,916 S 7/2013 Hoglund
8,491,644 B1 7/2013 Carson et al.
8,597,217 B2 12/2013 Lowe et al.
8,597,339 B2 12/2013 Augustine et al.
8,603,150 B2 12/2013 Kane et al.
8,632,576 B2 1/2014 Quisenberry
8,647,374 B2 2/2014 Koewler
8,715,330 B2 5/2014 Lowe et al.
8,778,119 B2 7/2014 Starr et al.
8,808,344 B2 8/2014 Scott et al.
8,840,581 B2 9/2014 McGill et al.
9,034,458 B2 5/2015 Li
9,078,742 B2 7/2015 Quincy, III et al.
9,089,462 B1 7/2015 Lafleche
9,211,358 B2 12/2015 Sinko et al.
9,278,024 B2 3/2016 Scott et al.
9,333,112 B2 5/2016 Carson
9,433,527 B2 9/2016 Varga et al.
9,552,706 B2 1/2017 Schneider et al.
9,566,185 B2 2/2017 Carson et al.
9,622,907 B2 4/2017 Carson et al.
9,642,404 B2 5/2017 Giles et al.
9,687,386 B2 6/2017 Carson
9,763,823 B2 9/2017 Voorhees et al.
9,907,889 B2 3/2018 Locke et al.
10,010,452 B2 7/2018 Wenske et al.
10,123,902 B2 11/2018 Carson et al.
10,220,198 B2 3/2019 Fuchs et al.
10,258,501 B2 4/2019 Carson
10,376,412 B2 8/2019 Brienza et al.
10,441,458 B2 10/2019 Voorhees et al.
10,441,707 B2 10/2019 Voorhees et al.
10,548,778 B2 2/2020 Hassenpflug et al.
10,610,424 B1 4/2020 Hoover
D887,426 S 6/2020 Matsushita
10,912,672 B1 2/2021 Jones et al.
D922,424 S 6/2021 Frueh et al.
D925,574 S 7/2021 Beko
D928,188 S 8/2021 Giannino et al.
11,173,071 B1 11/2021 Tawil et al.
D939,550 S 12/2021 Miyai et al.
11,234,859 B2 2/2022 Voorhees et al.
D947,216 S 3/2022 Leininger
11,285,039 B2 * 3/2022 Steele .................. F24F 5/0035
D948,534 S 4/2022 Bessette et al.
D952,666 S 5/2022 Sajan
D959,475 S 8/2022 Norman
D960,191 S 8/2022 Feit et al.
D973,067 S 12/2022 Oh et al.
11,975,123 B2 5/2024 Appel et al.
12,193,968 B2 1/2025 Voorhees et al.
2001/0034545 A1 10/2001 Elkins
2001/0039439 A1 11/2001 Elkins et al.
2002/0007203 A1 1/2002 Gilmartin et al.
2002/0015689 A1 2/2002 Munro et al.
2002/0019657 A1 2/2002 Elkins
2002/0107558 A1 8/2002 Clifton et al.

(56) References Cited

U.S. PATENT DOCUMENTS

| | | | |
|---|---|---|---|
| 2002/0111657 | A1 | 8/2002 | Dae et al. |
| 2002/0138121 | A1 | 9/2002 | Fox |
| 2002/0161419 | A1 | 10/2002 | Carson et al. |
| 2003/0074038 | A1 | 4/2003 | Gruszecki et al. |
| 2003/0078638 | A1 | 4/2003 | Voorhees et al. |
| 2003/0078639 | A1 | 4/2003 | Carson |
| 2003/0078640 | A1 | 4/2003 | Carson et al. |
| 2003/0109911 | A1 | 6/2003 | Lachenbruch et al. |
| 2003/0114903 | A1 | 6/2003 | Ellingboe |
| 2003/0135252 | A1 | 7/2003 | MacHold et al. |
| 2003/0149359 | A1 | 8/2003 | Smith |
| 2003/0149461 | A1 | 8/2003 | Johnson |
| 2003/0150232 | A1 | 8/2003 | Brudnicki |
| 2003/0163179 | A1 | 8/2003 | Hoglund et al. |
| 2003/0163180 | A1 | 8/2003 | Hoglund et al. |
| 2003/0163183 | A1 | 8/2003 | Carson |
| 2003/0163185 | A1 | 8/2003 | Carson |
| 2003/0212416 | A1 | 11/2003 | Cinelli et al. |
| 2004/0030372 | A1 | 2/2004 | Ellingboe et al. |
| 2004/0030373 | A1 | 2/2004 | Ellingboe et al. |
| 2004/0059212 | A1 | 3/2004 | Abreu |
| 2004/0064170 | A1 | 4/2004 | Radons et al. |
| 2004/0064171 | A1 | 4/2004 | Briscoe et al. |
| 2004/0073280 | A1 | 4/2004 | Dae et al. |
| 2004/0082886 | A1 | 4/2004 | Timpson |
| 2004/0087606 | A1 | 5/2004 | Voorhees et al. |
| 2004/0133253 | A1 | 7/2004 | Grahn et al. |
| 2004/0158303 | A1 | 8/2004 | Lennox et al. |
| 2004/0225341 | A1 | 11/2004 | Schock et al. |
| 2004/0243122 | A1 | 12/2004 | Auth et al. |
| 2004/0252750 | A1 | 12/2004 | Gruszecki et al. |
| 2004/0255362 | A1 | 12/2004 | Soerens et al. |
| 2004/0260369 | A1 | 12/2004 | Schock et al. |
| 2004/0267339 | A1 | 12/2004 | Yon et al. |
| 2005/0028551 | A1 | 2/2005 | Noda et al. |
| 2005/0060012 | A1 | 3/2005 | Voorhees et al. |
| 2005/0065583 | A1 | 3/2005 | Voorhees et al. |
| 2005/0096714 | A1 | 5/2005 | Freedman et al. |
| 2005/0177212 | A1 | 8/2005 | Njemanze |
| 2005/0187502 | A1 | 8/2005 | Krempel et al. |
| 2005/0244629 | A1 | 11/2005 | Usui et al. |
| 2005/0288749 | A1 | 12/2005 | Lachenbruch |
| 2006/0024053 | A1 | 2/2006 | Grant |
| 2006/0030916 | A1 | 2/2006 | Lennox |
| 2006/0036304 | A1 | 2/2006 | Cordani et al. |
| 2006/0058858 | A1 | 3/2006 | Smith |
| 2006/0069418 | A1 | 3/2006 | Schock et al. |
| 2006/0074469 | A1 | 4/2006 | Lennox et al. |
| 2006/0122673 | A1 | 6/2006 | Callister et al. |
| 2006/0124141 | A1 | 6/2006 | Dobak |
| 2006/0136023 | A1 | 6/2006 | Dobak |
| 2006/0161232 | A1 | 7/2006 | Kasza et al. |
| 2006/0190066 | A1 | 8/2006 | Worthen |
| 2006/0235114 | A1 | 10/2006 | Kitazono et al. |
| 2006/0247744 | A1 | 11/2006 | Nest et al. |
| 2006/0276089 | A1 | 12/2006 | Amarasinghe et al. |
| 2006/0287697 | A1 | 12/2006 | Lennox |
| 2006/0293734 | A1 | 12/2006 | Scott et al. |
| 2007/0016270 | A1 | 1/2007 | Stelea et al. |
| 2007/0043409 | A1 | 2/2007 | Brian et al. |
| 2007/0049997 | A1 | 3/2007 | Fields et al. |
| 2007/0054122 | A1 | 3/2007 | Paisner et al. |
| 2007/0068931 | A1 | 3/2007 | Augustine et al. |
| 2007/0073368 | A1 | 3/2007 | Cazzini et al. |
| 2007/0100404 | A1 | 5/2007 | Ko et al. |
| 2007/0173735 | A1 | 7/2007 | Callister et al. |
| 2007/0213793 | A1 | 9/2007 | Hayes |
| 2007/0225782 | A1 | 9/2007 | Taylor |
| 2007/0244475 | A1 | 10/2007 | Carson et al. |
| 2007/0270925 | A1 | 11/2007 | Levinson |
| 2008/0027523 | A1 | 1/2008 | Behringer et al. |
| 2008/0046046 | A1 | 2/2008 | Ginsburg |
| 2008/0114431 | A1 | 5/2008 | Ginsburg |
| 2008/0147152 | A1 | 6/2008 | Quincy et al. |
| 2008/0249524 | A1 | 10/2008 | Dunning |
| 2008/0255644 | A1 | 10/2008 | Carson |
| 2008/0269852 | A1 | 10/2008 | Lennox et al. |
| 2008/0275534 | A1 | 11/2008 | Noel |
| 2009/0018504 | A1 | 1/2009 | Pile-Spellman et al. |
| 2009/0043366 | A1 | 2/2009 | Dae |
| 2009/0066079 | A1 | 3/2009 | Miros et al. |
| 2009/0088825 | A1 | 4/2009 | Ota |
| 2009/0099629 | A1 | 4/2009 | Carson et al. |
| 2009/0131835 | A1 | 5/2009 | Voorhees et al. |
| 2009/0149925 | A1 | 6/2009 | MacDonald et al. |
| 2009/0157000 | A1 | 6/2009 | Waller |
| 2009/0177184 | A1 | 7/2009 | Christensen et al. |
| 2009/0182400 | A1 | 7/2009 | Dae et al. |
| 2009/0228082 | A1 | 9/2009 | Ross, III et al. |
| 2009/0250367 | A1 | 10/2009 | Murdoch et al. |
| 2009/0280182 | A1 | 11/2009 | Beck et al. |
| 2009/0287283 | A1 | 11/2009 | Biser et al. |
| 2009/0299287 | A1 | 12/2009 | Carson et al. |
| 2009/0312823 | A1 | 12/2009 | Patience et al. |
| 2009/0326619 | A1 | 12/2009 | Kagan |
| 2010/0016933 | A1 | 1/2010 | Chen et al. |
| 2010/0137951 | A1 | 6/2010 | Lennox et al. |
| 2010/0168825 | A1 | 7/2010 | Barbknecht |
| 2010/0198122 | A1 | 8/2010 | Freund |
| 2010/0198320 | A1 | 8/2010 | Pierre et al. |
| 2010/0204765 | A1 | 8/2010 | Hall et al. |
| 2010/0217260 | A1 | 8/2010 | Aramayo |
| 2010/0241073 | A1 | 9/2010 | Andersen et al. |
| 2010/0312160 | A1 | 12/2010 | Creighton et al. |
| 2010/0312202 | A1 | 12/2010 | Henley et al. |
| 2011/0021960 | A1 | 1/2011 | Filtvedt et al. |
| 2011/0029051 | A1 | 2/2011 | Ross |
| 2011/0045056 | A1 | 2/2011 | Munro et al. |
| 2011/0098792 | A1 | 4/2011 | Lowe et al. |
| 2011/0125238 | A1 | 5/2011 | Nofzinger |
| 2011/0152982 | A1 | 6/2011 | Richardson |
| 2011/0166633 | A1 | 7/2011 | Stull |
| 2011/0172749 | A1 | 7/2011 | Christensen et al. |
| 2011/0172750 | A1 | 7/2011 | Cassidy et al. |
| 2011/0306972 | A1 | 12/2011 | Widenhouse et al. |
| 2011/0307040 | A1 | 12/2011 | Peterson |
| 2011/0308781 | A1 | 12/2011 | O'Riordan et al. |
| 2011/0313497 | A1 | 12/2011 | Mcfarlane |
| 2012/0046720 | A1 | 2/2012 | Ishizaki |
| 2012/0065715 | A1 | 3/2012 | Carson |
| 2012/0080031 | A1 | 4/2012 | Belson |
| 2012/0095536 | A1 | 4/2012 | Machold et al. |
| 2012/0172774 | A1 | 7/2012 | Lowe et al. |
| 2012/0185021 | A1 | 7/2012 | Johnson et al. |
| 2012/0191035 | A1 | 7/2012 | Stephan |
| 2012/0204881 | A1 | 8/2012 | Davidson et al. |
| 2012/0220960 | A1 | 8/2012 | Ruland |
| 2012/0288848 | A1 | 11/2012 | Latham et al. |
| 2013/0006335 | A1 | 1/2013 | Lowe |
| 2013/0023808 | A1 | 1/2013 | Brown et al. |
| 2013/0116760 | A1* | 5/2013 | Carson ...................... A61F 7/10 607/104 |
| 2013/0138185 | A1 | 5/2013 | Paxman et al. |
| 2013/0190667 | A1 | 7/2013 | Kane et al. |
| 2013/0238042 | A1 | 9/2013 | Gildersleeve et al. |
| 2013/0238043 | A1 | 9/2013 | Beardall et al. |
| 2013/0310725 | A1 | 11/2013 | Jerrells et al. |
| 2014/0039451 | A1 | 2/2014 | Bangera et al. |
| 2014/0046411 | A1 | 2/2014 | Elkins et al. |
| 2014/0172050 | A1 | 6/2014 | Dabrowiak |
| 2014/0214138 | A1 | 7/2014 | Voorhees et al. |
| 2014/0222121 | A1 | 8/2014 | Spence et al. |
| 2014/0228717 | A1 | 8/2014 | Parish et al. |
| 2014/0228918 | A1 | 8/2014 | Brienza et al. |
| 2014/0276253 | A1 | 9/2014 | Varga et al. |
| 2014/0277301 | A1 | 9/2014 | Varga et al. |
| 2014/0288621 | A1 | 9/2014 | Efremkin |
| 2014/0316494 | A1 | 10/2014 | Augustine et al. |
| 2014/0343639 | A1 | 11/2014 | Hopper et al. |
| 2015/0025606 | A1 | 1/2015 | Davis |
| 2015/0051673 | A1 | 2/2015 | Rivas Tapia |
| 2015/0119963 | A1 | 4/2015 | Cosse |
| 2015/0173942 | A1 | 6/2015 | Whitely |
| 2015/0209174 | A1 | 7/2015 | Abreu |

(56) References Cited

U.S. PATENT DOCUMENTS

| | | | |
|---|---|---|---|
| 2015/0209192 | A1 | 7/2015 | Manion et al. |
| 2015/0223972 | A1 | 8/2015 | Dabrowiak |
| 2015/0230973 | A1 | 8/2015 | Dabrowiak et al. |
| 2015/0231009 | A1 | 8/2015 | Lewis |
| 2015/0250643 | A1 | 9/2015 | Paradis |
| 2015/0290042 | A1 | 10/2015 | Freer et al. |
| 2015/0366703 | A1 | 12/2015 | Du |
| 2015/0373781 | A1 | 12/2015 | Augustine et al. |
| 2015/0374045 | A1 | 12/2015 | Codner et al. |
| 2016/0008166 | A1 | 1/2016 | Voorhees et al. |
| 2016/0022477 | A1 | 1/2016 | Schaefer et al. |
| 2016/0038336 | A1 | 2/2016 | Hilton et al. |
| 2016/0310316 | A1 | 10/2016 | Hixson, Jr. |
| 2016/0324683 | A1 | 11/2016 | Carson |
| 2017/0049618 | A1 | 2/2017 | Ward et al. |
| 2017/0135855 | A1 | 5/2017 | Stefan et al. |
| 2017/0151087 | A1 | 6/2017 | Carson et al. |
| 2017/0189225 | A1 | 7/2017 | Voorhees et al. |
| 2017/0209305 | A1 | 7/2017 | Kaforey et al. |
| 2017/0224528 | A1 | 8/2017 | Berg et al. |
| 2017/0246029 | A1 | 8/2017 | Clark |
| 2017/0246031 | A1 | 8/2017 | Benyaminpour et al. |
| 2017/0246374 | A1 | 8/2017 | Voorhees et al. |
| 2017/0348144 | A1 | 12/2017 | Taylor et al. |
| 2017/0348145 | A1 | 12/2017 | Voorhees et al. |
| 2017/0354534 | A1 | 12/2017 | Paradis et al. |
| 2018/0000255 | A1 | 1/2018 | Youngblood et al. |
| 2018/0014967 | A1 | 1/2018 | Taylor |
| 2018/0042762 | A1 | 2/2018 | Galer |
| 2018/0042763 | A1 | 2/2018 | Galer et al. |
| 2018/0064594 | A1 | 3/2018 | Finch, Jr. et al. |
| 2018/0140407 | A1 | 5/2018 | Yoskowitz |
| 2018/0207024 | A1 | 7/2018 | Dabrowiak et al. |
| 2018/0214297 | A1 | 8/2018 | Hughett et al. |
| 2018/0214302 | A1 | 8/2018 | Dabrowiak et al. |
| 2018/0263677 | A1 | 9/2018 | Hilton et al. |
| 2018/0263748 | A1 | 9/2018 | Quinn |
| 2018/0295980 | A1 | 10/2018 | Boersma et al. |
| 2018/0376539 | A1 | 12/2018 | Augustine et al. |
| 2019/0083322 | A1 | 3/2019 | Huang et al. |
| 2019/0085644 | A1 | 3/2019 | Ames et al. |
| 2019/0099288 | A1 | 4/2019 | Vergara et al. |
| 2019/0117446 | A1 | 4/2019 | Carson et al. |
| 2019/0192337 | A1 | 6/2019 | Taylor et al. |
| 2019/0201574 | A1 | 7/2019 | Delury et al. |
| 2019/0262169 | A1 | 8/2019 | Vergara et al. |
| 2019/0328576 | A1 | 10/2019 | Lowe et al. |
| 2019/0331277 | A1 | 10/2019 | Vachon |
| 2020/0001022 | A1 | 1/2020 | Landy, III et al. |
| 2020/0071051 | A1 | 3/2020 | Lewis |
| 2020/0129326 | A1 | 4/2020 | Sinha et al. |
| 2020/0155341 | A1 | 5/2020 | Voorhees et al. |
| 2020/0214471 | A1 | 7/2020 | Paperno |
| 2020/0246180 | A1 | 8/2020 | Liang et al. |
| 2020/0289361 | A1 | 9/2020 | Tian et al. |
| 2020/0345971 | A1 | 11/2020 | Schirm et al. |
| 2020/0405530 | A1 | 12/2020 | Taylor et al. |
| 2021/0060230 | A1 | 3/2021 | Hopper et al. |
| 2021/0123641 | A1 | 4/2021 | Monazami et al. |
| 2022/0087874 | A1 | 3/2022 | Schneider et al. |
| 2022/0151821 | A1 | 5/2022 | Voorhees et al. |
| 2022/0192865 | A1 | 6/2022 | Hughett, Sr. et al. |
| 2022/0192867 | A1 | 6/2022 | Stich et al. |
| 2022/0233344 | A1 | 7/2022 | Hoglund |
| 2022/0233347 | A1 | 7/2022 | Canary et al. |
| 2022/0265468 | A1 | 8/2022 | Xu et al. |
| 2022/0280336 | A1 | 9/2022 | Smith et al. |
| 2022/0287875 | A1 | 9/2022 | Minchew et al. |
| 2022/0287876 | A1 | 9/2022 | Smith et al. |
| 2022/0296413 | A1 | 9/2022 | Jones |
| 2022/0296414 | A1 | 9/2022 | Bible et al. |
| 2022/0304847 | A1 | 9/2022 | Kuroda et al. |
| 2022/0313478 | A1 | 10/2022 | Johnston et al. |
| 2022/0331153 | A1 | 10/2022 | Xie et al. |
| 2022/0347009 | A1 | 11/2022 | Hughett, Sr. et al. |
| 2022/0401259 | A1 | 12/2022 | Basciano et al. |
| 2022/0406017 | A1 | 12/2022 | Wang et al. |
| 2023/0000668 | A1 | 1/2023 | Walker et al. |
| 2023/0009524 | A1 | 1/2023 | Johnston et al. |
| 2023/0011631 | A1 | 1/2023 | Yin et al. |
| 2023/0019048 | A1 | 1/2023 | Stich et al. |
| 2023/0021245 | A1 | 1/2023 | Walker et al. |
| 2023/0040583 | A1 | 2/2023 | Falis et al. |
| 2023/0077318 | A9 | 3/2023 | Voorhees et al. |
| 2023/0190519 | A1 | 6/2023 | Stich et al. |
| 2023/0346630 | A1 | 11/2023 | Lowe et al. |
| 2023/0414445 | A1 | 12/2023 | Sundar et al. |
| 2024/0065884 | A1 | 2/2024 | Fallows et al. |
| 2024/0082052 | A1 | 3/2024 | Cho et al. |
| 2024/0091054 | A1 | 3/2024 | Boone-Worthman et al. |
| 2024/0099878 | A1 | 3/2024 | Voorhees et al. |
| 2024/0366422 | A1 | 11/2024 | Johnston et al. |
| 2025/0032310 | A1 | 1/2025 | Stich et al. |
| 2025/0041107 | A1 | 2/2025 | Walker et al. |
| 2025/0110628 | A1 | 4/2025 | Litman et al. |
| 2025/0134705 | A1 | 5/2025 | Stich et al. |
| 2025/0143918 | A1 | 5/2025 | Voorhees et al. |
| 2025/0161107 | A1 | 5/2025 | Stich et al. |
| 2025/0198550 | A1 | 6/2025 | Johnston et al. |
| 2025/0332025 | A1 | 10/2025 | Brooks et al. |
| 2026/0026965 | A1 | 1/2026 | Xu et al. |
| 2026/0102279 | A1 | 4/2026 | Canary et al. |
| 2026/0174591 | A1 | 6/2026 | Johnston et al. |

FOREIGN PATENT DOCUMENTS

| | | | |
|---|---|---|---|
| CA | 2729122 | A1 | 7/2002 |
| CA | 2193385 | C | 9/2006 |
| CN | 102026596 | A | 4/2011 |
| CN | 101389372 | B | 8/2012 |
| CN | 102746518 | A | 10/2012 |
| CN | 103939695 | B | 3/2016 |
| CN | 305928532 | | 7/2020 |
| CN | 111643265 | A | 9/2020 |
| CN | 306402573 | | 3/2021 |
| CN | 113230017 | A | 8/2021 |
| CN | 307690236 | | 11/2022 |
| CN | 309180016 | | 3/2025 |
| DE | 102014118510 | A1 | 6/2016 |
| EP | 0862901 | A1 | 9/1998 |
| EP | 1073388 | A1 | 2/2001 |
| EP | 1616543 | A2 | 1/2006 |
| EP | 1641503 | A2 | 4/2006 |
| EP | 1718894 | B1 | 7/2010 |
| EP | 2204150 | A1 | 7/2010 |
| EP | 2269546 | A1 | 1/2011 |
| GB | 2118440 | A | 11/1983 |
| JP | H09508045 | A | 8/1997 |
| JP | 2002534160 | A | 10/2002 |
| JP | 2007029638 | A | 2/2007 |
| JP | 2013248293 | A | 12/2013 |
| KR | 20110020420 | A | 3/2011 |
| WO | 9807397 | A1 | 2/1998 |
| WO | 9831310 | A1 | 7/1998 |
| WO | 199944552 | A1 | 9/1999 |
| WO | 9953874 | A1 | 10/1999 |
| WO | 2000040185 | A1 | 7/2000 |
| WO | 2003086253 | A2 | 10/2003 |
| WO | 2004075949 | A2 | 9/2004 |
| WO | 2005028984 | A1 | 3/2005 |
| WO | 2005117546 | A2 | 12/2005 |
| WO | 2007120677 | A2 | 10/2007 |
| WO | 2009090403 | A1 | 7/2009 |
| WO | 2009147413 | A1 | 12/2009 |
| WO | 2009148636 | A1 | 12/2009 |
| WO | 2012125916 | A2 | 9/2012 |
| WO | 2012138980 | A2 | 10/2012 |
| WO | 2015084925 | A1 | 6/2015 |
| WO | 2016057119 | A1 | 4/2016 |
| WO | 2016123500 | A1 | 8/2016 |
| WO | 2017127768 | A1 | 7/2017 |
| WO | 2018075576 | A1 | 4/2018 |
| WO | 2022155130 | A1 | 7/2022 |
| WO | 2022155132 | A1 | 7/2022 |

(56) References Cited

FOREIGN PATENT DOCUMENTS

| | | | |
|---|---|---|---|
| WO | 2022159513 | A1 | 7/2022 |
| WO | 2022159879 | A1 | 7/2022 |
| WO | 2022165068 | A1 | 8/2022 |
| WO | 2022235513 | A1 | 11/2022 |
| WO | 2023121674 | A1 | 6/2023 |
| WO | 2023140870 | A1 | 7/2023 |
| WO | 2023154050 | A1 | 8/2023 |
| WO | 2023229609 | A1 | 11/2023 |

OTHER PUBLICATIONS

PCT/US2022/013569 filed Jan. 24, 2022 International Search Report and Written Opinion dated Aug. 29, 2022.
PCT/US2022/016020 filed Feb. 10, 2022 International Search Report and Written Opinion dated Oct. 31, 2022.
U.S. Appl. No. 17/848,074, filed Jun. 23, 2022 Advisory Action dated Jul. 9, 2024.
U.S. Appl. No. 17/848,074, filed Jun. 23, 2022 Final Office Action dated Apr. 26, 2024.
U.S. Appl. No. 17/848,074, filed Jun. 23, 2022 Non-Final Office Action dated Aug. 15, 2024.
U.S. Appl. No. 18/536,087, filed Dec. 11, 2023 Non-Final Office Action dated Jun. 28, 2024.
U.S. Appl. No. 18/536,087, filed Dec. 11, 2023 Notice of Allowance dated Aug. 29, 2024.
All in 1: Injection Tracker, posted date unavailable [online], [retrieved Apr. 10, 2025]. Retrieved from internet, https://apps.apple.com/us/app/all-in-1-injection-tracker/id1667540577. (Year: 2025).
Creating an accessible, usable and compelling Injection Site Tracking feature that can used by all our users, posted date May 2020 [u online], [retrieved Apr. 10, 2025]. Retrieved from internet, https://www.bradstricker.com/case-studies/injection-site-tracking. (Year: 2020).
Injection Tracker App, posted date unavailable [online], [retrieved Apr. 10, 2025]. Retrieved from internet, https://www.vladcristei.com/project_page_it. (Year: 2025).
U.S. Appl. No. 17/583,090, filed Jan. 24, 2022 Final Office Action dated Jul. 1, 2025.
U.S. Appl. No. 17/678,965, filed Feb. 23, 2022 Notice of Allowance dated Jun. 3, 2025.
U.S. Appl. No. 17/686,301, filed Mar. 3, 2022 Advisory Action dated Apr. 4, 2025.
U.S. Appl. No. 17/686,301, filed Mar. 3, 2022 Non-Final Office Action dated May 14, 2025.
U.S. Appl. No. 17/689,791, filed Mar. 8, 2022 Final Office Action dated May 21, 2025.
U.S. Appl. No. 17/690,908, filed Mar. 9, 2022 Final Office Action dated Jun. 24, 2025.
U.S. Appl. No. 17/694,416, filed Mar. 14, 2022 Final Office Action dated Jun. 20, 2025.
U.S. Appl. No. 17/700,216, filed Mar. 21, 2022 Final Office Action dated Jun. 23, 2025.
U.S. Appl. No. 17/709,019, filed Mar. 30, 2022 Final Office Action dated Jun. 15, 2025.
U.S. Appl. No. 17/723,210, filed Apr. 18, 2022 Final Office Action dated May 21, 2025.
U.S. Appl. No. 17/849,419, filed Jun. 24, 2022 Non-Final Office Action dated Jun. 13, 2025.
U.S. Appl. No. 17/857,997, filed Jul. 5, 2022 Non-Final Office Action dated Apr. 28, 2025.
U.S. Appl. No. 17/881,270, filed Aug. 4, 2022 Non-Final Office Action dated Apr. 28, 2025.
U.S. Appl. No. 18/085,566, filed Dec. 20, 2022 Restriction Requirement dated May 16, 2025.
U.S. Appl. No. 29/939,277, filed Apr. 25, 2024 Non-Final Office Action dated May 13, 2025.
Wound care app can help determine appropriate wounddressings, posted date Apr. 24, 2013 [online], [retrieved Apr. 10, 2025]. Retrieved from internet, https://www.imedicalapps.com/2013/04/wound-care-app-dressings/. (Year: 2013).
Advantage Engineering, "Proper Use of Inhibited Propylene Glycol", Jun. 12, 2001, http://www.ttequip.com/knowledgelibrary/Proper%20Use%20Of%20Inh- ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g- us.edu/hbase/tables.thron.html Jul. 31, 2010.
Murray, R. Z., et al. "Development and use of biomaterials as wound healing therapies" Burns & Trauma (2019) 7:2 https://doi.org/10.1186/s41038-018-0139-7 (2019).
P21TUS2022011971 filed Jan. 11, 2022 International Search Report and Written Opinion dated Apr. 21, 2022.
PCT/US2015/045548 filed Aug. 17, 2015 International Search Report and Written Opinion dated Nov. 24, 2015.
PCT/US2016/015688 filed Jan. 29, 2016 International Search Report and Written Opinion dated Apr. 1, 2016.
PCT/US2022/011980 filed Jan. 11, 2022 International Search Report and Written Opinion dated Apr. 13, 2022.
PCT/US2022/013007 filed Jan. 19, 2022 International Search Report and Written Opinion dated Apr. 22, 2022.
PCT/US2022/013672 filed Jan. 25, 2022, International Search Report and Written Opinion dated Jul. 15, 2022.
PCT/US2022/014147 filed Jan. 27, 2022 International Search Report and Written Opinion dated Jul. 18, 2022.
Sevgi, M., et al. "Topical Antimicrobials for Burn Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021.
U.S. Appl. No. 17/589,849, filed Jan. 31, 2022 Final Office Action dated Jun. 27, 2023.
U.S. Appl. No. 17/589,849, filed Jan. 31, 2022 Non-Final Office Action dated Apr. 12, 2023.
PCT/US2022/031428 filed May 27, 2022 International Search Report and Written Opinion dated Jan. 30, 2023.
U.S. Appl. No. 17/547,128, filed Dec. 9, 2021 Non-Final Office Action dated Feb. 10, 2025.
U.S. Appl. No. 17/552,309, filed Dec. 15, 2021 Non-Final Office Action dated Mar. 14, 2025.
U.S. Appl. No. 17/552,309, filed Dec. 15, 2021 Restriction Requirement dated Dec. 12, 2024.
U.S. Appl. No. 17/583,090, filed Jan. 24, 2022 Non-Final Office Action dated Feb. 13, 2025.
U.S. Appl. No. 17/584,101, filed Jan. 25, 2022 Non-Final Office Action dated Feb. 5, 2025.
U.S. Appl. No. 17/678,965, filed Feb. 23, 2022 Non-Final Office Action dated Feb. 12, 2025.
U.S. Appl. No. 17/686,301, filed Mar. 3, 2022 Final Office Action dated Jan. 29, 2025.
U.S. Appl. No. 17/689,791, filed Mar. 8, 2022 Non-Final Office Action dated Dec. 30, 2024.
U.S. Appl. No. 17/690,908, filed Mar. 9, 2022 Non-Final Office Action dated Dec. 18, 2024.
U.S. Appl. No. 17/691,990, filed Mar. 10, 2022 Non-Final Office Action dated Dec. 17, 2024.
U.S. Appl. No. 17/694,416, filed Mar. 14, 2022 Non-Final Office Action dated Jan. 22, 2025.
U.S. Appl. No. 17/700,216, filed Mar. 21, 2022 Non-Final Office Action dated Feb. 5, 2025.
U.S. Appl. No. 17/709,019, filed Mar. 30, 2022 Non-Final Office Action dated Dec. 31, 2024.
U.S. Appl. No. 17/723,210, filed Apr. 18, 2022 Non-Final Office Action dated Dec. 20, 2024.

(56) References Cited

OTHER PUBLICATIONS

U.S. Appl. No. 17/849,419, filed Jun. 24, 2022 Final Office Action dated Feb. 14, 2025.
U.S. Appl. No. 17/857,997, filed Jul. 5, 2022 Restriction Requirement dated Feb. 12, 2025.
U.S. Appl. No. 17/859,995, filed Jul. 7, 2022 Non-Final Office Action dated Mar. 11, 2025.
U.S. Appl. No. 17/881,270, filed Aug. 4, 2022 Restriction Requirement dated Feb. 11, 2025.
PCT/US2022/026999 filed Apr. 29, 2022 International Search Report and Written Opinion dated Oct. 24, 2022.
U.S. Appl. No. 17/589,849, filed Jan. 31, 2022 Notice of Allowance dated Aug. 23, 2023.
U.S. Appl. No. 17/848,074, filed Jun. 23, 2022 Non-Final Office Action dated Nov. 30, 2023.
U.S. Appl. No. 17/547,128, filed Dec. 9, 2021 Restriction Requirement dated Sep. 5, 2024.
U.S. Appl. No. 17/583,090, filed Jan. 24, 2022 Restriction Requirement dated Sep. 6, 2024.
U.S. Appl. No. 17/584,101, filed Jan. 25, 2022 Restriction Requirement dated Nov. 5, 2024.
U.S. Appl. No. 17/686,301, filed Mar. 3, 2022 Non-Final Office Action dated Oct. 1, 2024.
U.S. Appl. No. 17/689,791, filed Mar. 8, 2022 Restriction Requirement dated Oct. 16, 2024.
U.S. Appl. No. 17/691,990, filed Mar. 10, 2022 Restriction Requirement dated Oct. 16, 2024.
U.S. Appl. No. 17/694,416, filed Mar. 14, 2022 Restriction Requirement dated Nov. 8, 2024.
U.S. Appl. No. 17/709,019, filed Mar. 30, 2022 Restriction Requirement dated Oct. 16, 2024.
U.S. Appl. No. 17/723,210, filed Apr. 18, 2022 Restriction Requirement dated Oct. 16, 2024.
U.S. Appl. No. 17/848,074, filed Jun. 23, 2022 Notice of Allowance dated Nov. 26, 2024.
U.S. Appl. No. 17/849,419, filed Jun. 24, 2022 Non-Final Office Action dated Nov. 8, 2024.
Lustig et al. "Solute Diffusion in Swollen Membranes. IX. Scaling Laws for Solute Diffusion in Gels", Journal of Applied Polymer Science, vol. 36, pp. 735-747 (Year: 1988).
U.S. Appl. No. 17/547,128, filed Dec. 9, 2021 Advisory Action dated Nov. 19, 2025.
U.S. Appl. No. 17/547,128, filed Dec. 9, 2021 Final Office Action dated Aug. 27, 2025.
U.S. Appl. No. 17/547,128, filed Dec. 9, 2021 Non-Final Office Action dated Dec. 29, 2025.
U.S. Appl. No. 17/552,309, filed Dec. 15, 2021 Advisory Action dated Oct. 2, 2025.
U.S. Appl. No. 17/552,309, filed Dec. 15, 2021 Final Office Action dated Jul. 30, 2025.
U.S. Appl. No. 17/552,309, filed Dec. 15, 2021 Non-Final Office Action dated Nov. 5, 2025.
U.S. Appl. No. 17/583,090, filed Jan. 24, 2022 Notice of Allowance dated Sep. 30, 2025.
U.S. Appl. No. 17/584,101, filed Jan. 25, 2022 Final Office Action dated Oct. 23, 2025.
U.S. Appl. No. 17/686,301, filed Mar. 3, 2022 Final Office Action dated Oct. 28, 2025.
U.S. Appl. No. 17/689,791, filed Mar. 8, 2022 Advisory Action dated Jul. 24, 2025.
U.S. Appl. No. 17/689,791, filed Mar. 8, 2022 Non-Final Office Action dated Nov. 5, 2025.
U.S. Appl. No. 17/690,908, filed Mar. 9, 2022 Advisory Action dated Sep. 3, 2025.
U.S. Appl. No. 17/690,908, filed Mar. 9, 2022 Non-Final Office Action dated Oct. 2, 2025.
U.S. Appl. No. 17/691,990, filed Mar. 10, 2022 Advisory Action dated Jul. 24, 2025.
U.S. Appl. No. 17/691,990, filed Mar. 10, 2022 Non-Final Office Action dated Aug. 28, 2025.
U.S. Appl. No. 17/694,416, filed Mar. 14, 2022 Advisory Action dated Aug. 20, 2025.
U.S. Appl. No. 17/694,416, filed Mar. 14, 2022 Non-Final Office Action dated Oct. 1, 2025.
U.S. Appl. No. 17/697,879, filed Mar. 17, 2022 Non-Final Office Action dated Sep. 30, 2025.
U.S. Appl. No. 17/700,216, filed Mar. 21, 2022 Advisory Action dated Oct. 9, 2025.
U.S. Appl. No. 17/700,216, filed Mar. 21, 2022 Non-Final Office Action dated Dec. 3, 2025.
U.S. Appl. No. 17/709,019, filed Mar. 30, 2022 Advisory Action dated Jul. 24, 2025.
U.S. Appl. No. 17/709,019, filed Mar. 30, 2022 Non-Final Office Action dated Nov. 19, 2025.
U.S. Appl. No. 17/723,210, filed Apr. 18, 2022 Advisory Action dated Jul. 31, 2025.
U.S. Appl. No. 17/723,210, filed Apr. 18, 2022 Non-Final Office Action dated Dec. 29, 2025.
U.S. Appl. No. 17/837,956, filed Jun. 10, 2022 Non-Final Office Action dated Nov. 3, 2025.
U.S. Appl. No. 17/848,039, filed Jun. 23, 2021 Non-Final Office Action dated Jul. 29, 2025.
U.S. Appl. No. 17/848,039, filed Jun. 23, 2022 Final Office Action dated Dec. 29, 2025.
U.S. Appl. No. 17/857,997, filed Jul. 5, 2022 Final Office Action dated Oct. 27, 2025.
U.S. Appl. No. 17/859,995, filed Jul. 7, 2022 Advisory Action dated Oct. 28, 2025.
U.S. Appl. No. 17/859,995, filed Jul. 7, 2022 Final Office Action dated Aug. 22, 2025.
U.S. Appl. No. 17/859,995, filed Jul. 7, 2022 Non-Final Office Action dated Dec. 23, 2025.
U.S. Appl. No. 17/881,270, filed Aug. 4, 2022 Final Office Action dated Oct. 27, 2025.
U.S. Appl. No. 18/085,566, filed Dec. 20, 2022 Non-Final Office Action dated Oct. 1, 2025.
U.S. Appl. No. 18/272,026, filed Jul. 12, 2023 Non-Final Office Action dated Jul. 31, 2025.
U.S. Appl. No. 18/273,163, filed Jul. 19, 2023 Restriction Requirement dated Nov. 6, 2025.
U.S. Appl. No. 18/274,156, filed Jul. 25, 2023 Non-Final Office Action dated Oct. 1, 2025.
U.S. Appl. No. 18/289,341, filed Nov. 2, 2023 Restriction Requirement dated Nov. 6, 2025.
U.S. Appl. No. 19/068,969, filed Mar. 3, 2025 Non-Final Office Action dated Dec. 29, 2025.
U.S. Appl. No. 29/939,277, filed Apr. 25, 2024 Restriction Requirement dated Oct. 2, 2025.
U.S. Appl. No. 17/547,128, filed Dec. 9, 2021 Final Office Action dated Apr. 6, 2026.
U.S. Appl. No. 17/686,301, filed Mar. 3, 2022 Non-Final Office Action dated Apr. 3, 2026.
U.S. Appl. No. 17/691,990, filed Mar. 10, 2022 Final Office Action dated Mar. 9, 2026.
U.S. Appl. No. 17/694,416, filed Mar. 14, 2022 Final Office Action dated Apr. 9, 2026.
U.S. Appl. No. 17/697,879, filed Mar. 17, 2022 Non-Final Office Action dated Mar. 26, 2026.
U.S. Appl. No. 17/837,956, filed Jun. 10, 2022 Final Office Action dated Feb. 24, 2026.
U.S. Appl. No. 17/848,039, filed Jun. 23, 2022 Notice of Allowance dated Apr. 13, 2026.
U.S. Appl. No. 17/849,419, filed Jun. 24, 2022 Notice of Allowance dated Jan. 29, 2026.
U.S. Appl. No. 18/085,566, filed Dec. 20, 2022 Final Office Action dated Mar. 9, 2026.
U.S. Appl. No. 18/272,026, filed Jul. 12, 2023 Notice of Allowance dated Mar. 27, 2026.
U.S. Appl. No. 18/272,332, filed Jul. 13, 2023 Non-Final Office Action dated Mar. 25, 2026.
U.S. Appl. No. 18/272,332, filed Jul. 13, 2023 Restriction Requirement dated Jan. 21, 2026.

(56) References Cited

OTHER PUBLICATIONS

U.S. Appl. No. 18/273,163, filed Jul. 19, 2023 Non-Final Office Action dated Feb. 3, 2026.
U.S. Appl. No. 18/274,156, filed Jul. 25, 2023 Final Office Action dated Mar. 25, 2026.
U.S. Appl. No. 18/289,341, filed Nov. 2, 2023 Non-Final Office Action dated Feb. 18, 2026.
U.S. Appl. No. 18/715,504, filed May 31, 2024 Non-Final Office Action dated Apr. 9, 2026.
U.S. Appl. No. 18/715,504, filed May 31, 2024 Restriction Requirement dated Feb. 4, 2026.
U.S. Appl. No. 29/939,277, filed Apr. 25, 2024 Ex Parte Quayle Action dated Feb. 23, 2026.
U.S. Appl. No. 17/552,309, filed Dec. 15, 2021 Final Office Action dated Apr. 22, 2026.
U.S. Appl. No. 17/584,101 filed Jan. 25, 2022 Non-Final Office Action dated May 14, 2026.
U.S. Appl. No. 17/689,791, filed Mar. 8, 2022 Final Office Action dated Apr. 22, 2026.
U.S. Appl. No. 17/690,908, filed Mar. 9, 2022 Final Office Action dated May 12, 2026.
U.S. Appl. No. 17/691,990, filed Mar. 10, 2022 Advisory Action dated May 27, 2026.
U.S. Appl. No. 17/691,990, filed Mar. 10, 2022 Non-Final Office Action dated Jun. 29, 2026.
U.S. Appl. No. 17/694,416, filed Mar. 14, 2022 Advisory Action dated Jun. 16, 2026.
U.S. Appl. No. 17/700,216, filed Mar. 21, 2022 Final Office Action dated Jun. 24, 2026.
U.S. Appl. No. 17/709,019, filed Mar. 30, 2022 Final Office Action dated Apr. 22, 2026.
U.S. Appl. No. 17/723,210, filed Apr. 18, 2022 Final Office Action dated May 5, 2026.
U.S. Appl. No. 17/837,956, filed Jun. 10, 2022 Notice of Allowance dated May 7, 2026.
U.S. Appl. No. 17/859,995, filed Jul. 7, 2022 Advisory Action dated Jul. 2, 2026.
U.S. Appl. No. 17/859,995, filed Jul. 7, 2022 Final Office Action dated Apr. 28, 2026.
U.S. Appl. No. 18/085,566, filed Dec. 20, 2022 Advisory Action dated May 14, 2026.
U.S. Appl. No. 18/085,566, filed Dec. 20, 2022 Notice of Allowance dated Jun. 17, 2026.
U.S. Appl. No. 18/274,156 filed Jul. 25, 2023 Notice of Allowance dated Jun. 9, 2026.
U.S. Appl. No. 18/832,782, filed Jul. 24, 2024 Non-Final Office Action dated Apr. 20, 2026.
U.S. Appl. No. 18/837,098, filed Aug. 8, 2024 Non-Final Office Action dated Apr. 22, 2026.
U.S. Appl. No. 18/866,907, filed Nov. 18, 2024 Non-Final Office Action dated Jun. 29, 2026.
U.S. Appl. No. 19/018,774, filed Jan. 13, 2025 Non-Final Office Action dated Jun. 18, 2026.
U.S. Appl. No. 19/068,969, filed Mar. 3, 2025 Non-Final Office Action dated Apr. 28, 2026.
U.S. Appl. No. 29/939,277, filed Apr. 25, 2024 Notice of Allowance dated Jun. 10, 2026.

* cited by examiner

FIG. 3
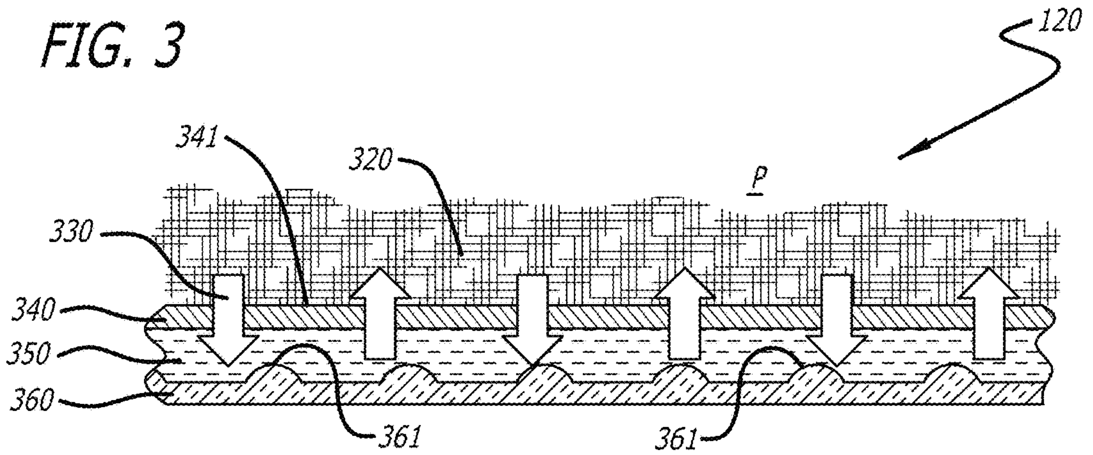
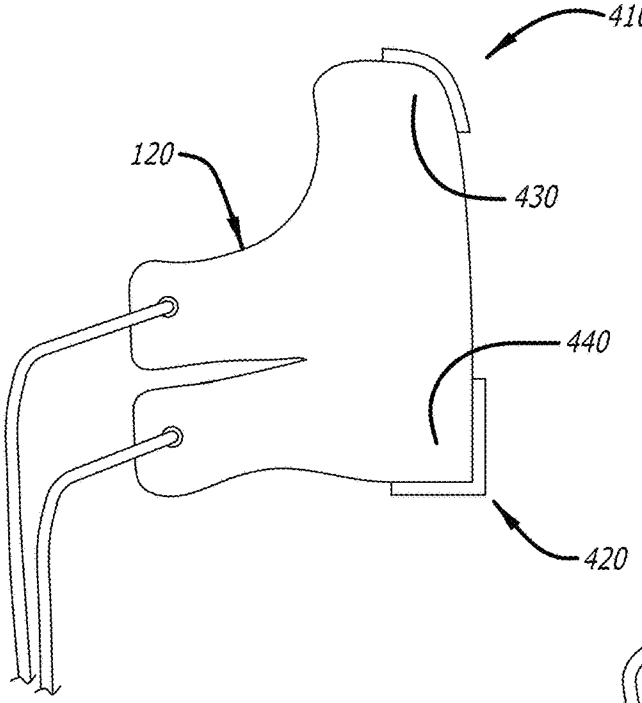
FIG. 4
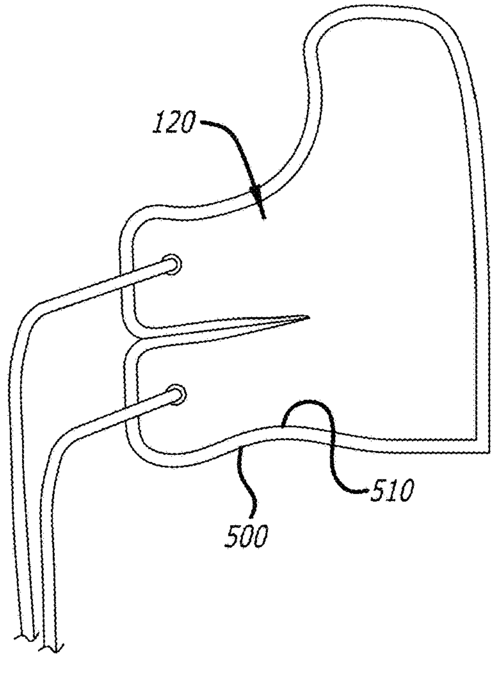
FIG. 5

SOFT BORDER FOR TARGETED TEMPERATURE MANAGEMENT

PRIORITY

This application is a U.S. national stage application of International Application No. PCT/US2022/014147, filed Jan. 27, 2022, which claims the benefit of priority to U.S. Provisional Application No. 63/142,397, filed Jan. 27, 2021, each of which is incorporated by reference in its entirety into this application.

SUMMARY

Briefly summarized, embodiments disclosed herein are directed to systems, methods and apparatuses for providing for a patient's comfort while undergoing Targeted Temperature Management (TTM), that is, cooling or heating a patient to provide medical benefits, such as neuroprotection following a stroke or surgery.

One problem that often arises with TTM systems is irritation of patients' skin due to pressure from an edge of the cooling and heating medical pads of the TTM system. Specifically, the medical pads may have a harsh edge, for example at curves or bends of the pads, that may cause discomfort and irritation for some patients. Even though the pads can contain a pliable material, like a hydrogel, that can conform to the patient's skin and provide good thermal contact, some patients may still experience skin irritation. In some cases, patients may use the pads for extended periods, exacerbating such discomfort and irritation after repeated contact. Embodiments of the disclosed apparatus and system can address this problem.

Disclosed herein is a medical pad for exchanging thermal energy with a patient body. The medical pad can comprise a flexible upper sheet, a flexible base member, an adhesive surface, and an edge guard. The flexible base member is interconnected to the flexible upper sheet to define a fluid containing layer between the flexible base member and the flexible upper sheet. The fluid containing layer comprises a plurality of tortuous fluid flow paths. The adhesive surface is disposed on a skin-contacting side of the flexible upper sheet, and is adapted for releasable adhesive contact with skin of the patient. The edge guard comprises a pliant shock-absorbent material surrounding a portion of an edge of the flexible upper sheet, and is configured to distribute pressure from the medical pad across a portion of the patient body in contact with a surface of the edge guard.

In some embodiments, the edge guard is configured to conduct thermal energy between the fluid containing layer and the patient.

In some embodiments, the pliant shock-absorbent material comprises silicone.

In some embodiments, the edge guard is disposed on the portion of the edge of the flexible upper sheet via an adhesive bond.

In some embodiments, the edge guard is locked on the portion of the edge of the flexible upper sheet via an attachment mechanism.

In some embodiments, the attachment mechanism comprises a convex member on an inside of the edge guard interlocking with a concave well on the portion of the edge of the flexible upper sheet.

In some embodiments, the convex member and the concave well are conical.

In some embodiments, the portion of the edge comprises at least a corner of the edge of the flexible upper sheet.

In some embodiments, the medical pad further comprises a conformable, thermally conductive layer of a hydrogel material.

In some embodiments, the flexible base member includes a plurality of dimples defining the plurality of tortuous fluid flow paths.

In some embodiments, the plurality of dimples are of a predetermined configuration comprising one or more of: a truncated cone configuration, a cylindrical configuration, or an elongated, truncated pyramid configuration.

In some embodiments, the plurality of dimples are arranged in a predetermined staggered pattern on an upper surface of the flexible base member, a lower smooth surface of the flexible upper sheet is supported at a plurality of points of contact with the dimples, and the dimples are staggered in at least two transverse directions on the upper surface of the flexible base member.

In some embodiments, the predetermined staggered pattern comprises offset rows and columns.

In some embodiments, the dimples within adjacent rows and adjacent columns are offset from one another by sixty degrees.

In some embodiments, the dimples are arranged in a herringbone pattern.

In some embodiments, the base member is formed to integrally define the plurality of dimples.

In some embodiments, the medical pad further comprises a filter disposed in line with a fluid flow path providing a fluid to the medical pad.

In some embodiments, the filter comprises a porous wall disposed parallel to a flow direction of the fluid along the fluid flow path.

In some embodiments, the filter is attached to the medical pad.

In some embodiments, the filter is disposed within the fluid containing layer of the medical pad.

Also disclosed herein is a medical pad for exchanging thermal energy with a patient body. The medical pad can comprise a flexible base member, a flexible film, a thermally conductive layer, an adhesive surface, and an edge guard. The flexible base member is of foam construction and has a plurality of integrally defined dimples. The flexible film is interconnected to the flexible base member to define a fluid containing layer between the flexible base member and the flexible film. The plurality of dimples define tortuous fluid flow paths within the fluid containing layer. The thermally conductive layer is laminated to one side of the flexible film. The adhesive surface is disposed on the thermally conductive layer. The adhesive surface is adapted for releasable adhesive contact with skin of a patient. The edge guard comprises a pliant shock-absorbent material surrounding a portion of an edge of the thermally conductive layer, and is configured to distribute pressure from the medical pad across a portion of the patient body in contact with a surface of the edge guard.

Also disclosed herein is a medical pad for contacting and exchanging thermal energy with a patient body. The medical pad can comprise a fluid containing layer, a fluid inlet, a fluid outlet, an adhesive surface, and an edge guard. The fluid containing layer contains a thermal exchange fluid configured to exchange thermal energy with the patient. The thermal exchange fluid transfers thermal energy to the patient while circulating within the fluid containing layer from the fluid inlet to the fluid outlet. The adhesive surface is disposed on a skin contacting side of the fluid containing layer, wherein thermal energy is exchangeable across the adhesive surface. The edge guard comprises a pliant shock-absorbent material surrounding a portion of an edge of the adhesive surface, and an edge guard adhesive layer disposed on a skin contacting side of the edge guard. The edge guard is configured to reduce pressure on the skin of the patient by distributing the pressure across a surface area of the edge guard. In some embodiments, a portion of the pliant shock-absorbent material is disposed between the adhesive surface and the patient body when in use Also disclosed herein is a medical pad edge guard for distributing pressure from an edge of a medical pad. The medical pad edge guard comprises an outer shell formed of a pliant shock-absorbent material. The medical pad edge guard further comprises an attachment mechanism configured to couple the medical pad edge guard to the edge of the medical pad.

In some embodiments, the attachment mechanism comprises an adhesive layer. In some embodiments, the attachment mechanism comprises a protrusion configured to engage with a recess portion of the medical pad. In some embodiments, the protrusion is disc-shaped and the recess portion is cylindrical. In some embodiments, the protrusion and the recess portion are substantially flat. In some embodiments, the protrusion and the recess portion are substantially conical. In some embodiments, the medical pad edge guard further comprises a portion disposed between the medical pad and skin of a patient. In some embodiments, the medical pad edge guard has a rounded shape or a rounded wedge shape, the portion disposed between the medical pad and the skin is rounded, and the rounded portion disposed between the medical pad and the skin is configured to protect the skin of the patient from roughness on the edge of the medical pad by distributing the pressure from the edge.

In some embodiments, the attachment mechanism comprises a second material different from the pliant shock-absorbent material of the outer shell, and the pliant shock-absorbent material of the outer shell is further configured to cushion skin of a patient by distributing pressure across a surface of the edge guard.

In some embodiments, the attachment mechanism comprises one or more of a protruding member comprising the second material, or a convex member comprising the second material. In some embodiments, the pliant shock-absorbent material of the outer shell comprises at least one of silicone, woven fabric, polyvinyl chloride (PVC), polyethylene, polyurethane, or latex. In some embodiments, the second material comprises silicone or vulcanized rubber. In some embodiments, the outer shell is at least partially filled with at least one of foam, cotton, mesh, polyester, wool or latex. In some embodiments, the medical pad edge guard is sized based on an outer circumference of the medical pad.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 3 illustrates a structure of an exemplary medical pad, according to some embodiments;

FIG. 4 illustrates an edge guard surrounding the perimeter of a medical pad, according to some embodiments;

FIG. 5 illustrates an edge guard surrounding the perimeter of a medical pad, according to some embodiments;

DETAILED DESCRIPTION

Figure 1:
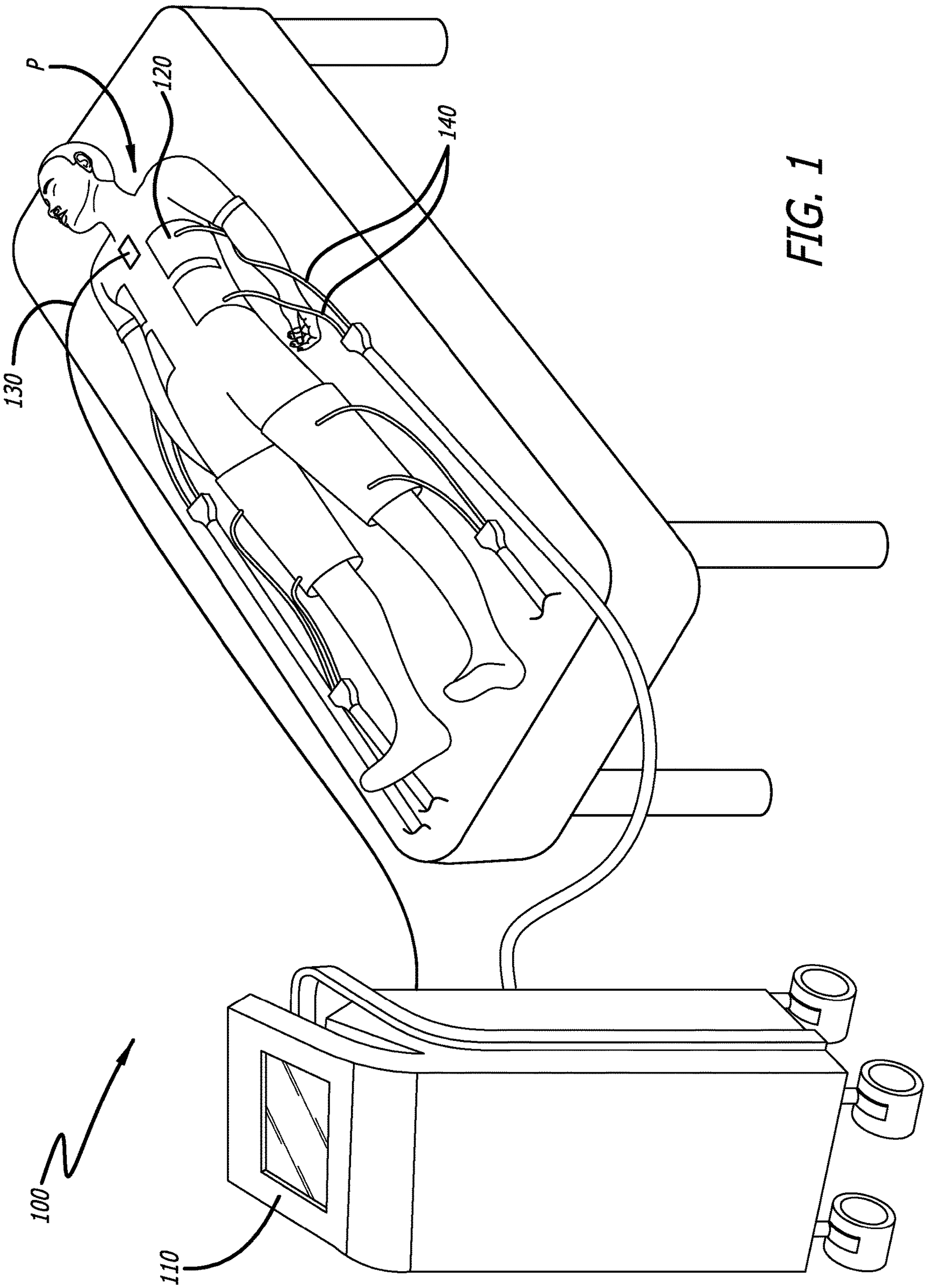
FIG. 1 illustrates a TTM system using medical pads for heating and/or cooling a patient, according to some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The effect of temperature variations on the human body has been well documented. Elevated temperatures may be harmful to the brain under normal conditions, and even more importantly, during periods of physical stress, such as illness or surgery. Conversely, lower body temperatures, or mild hypothermia, may offer some degree of neuroprotection. Moderate to profound hypothermia (below 32° C.) tends to be more harmful to the body and may lead to death.

Targeted Temperature Management (TTM) refers to cooling or heating a patient to provide medical benefits, such as neuroprotection following a stroke or surgery. TTM or thermoregulation can be viewed in two different ways. The first aspect of temperature management includes treating abnormal body temperatures, i.e. cooling the body from elevated temperatures (hyperthermia), or warming the body to manage hypothermia. Hypothermia may occur in response to exposure to cold environments, trauma, or long complex surgical procedures. Hyperthermia may occur in response to systemic inflammation, sepsis, stroke, or other brain injury.

The second aspect of thermoregulation is a treatment that employs techniques that physically control a patient's temperature to provide a physiological benefit, such as cooling for a degree of neuroprotection. Studies have shown that treatment with mild hypothermia, defined as lowering core body temperature 2-3° C., confers neuroprotection in stroke victims, and may hasten neurologic recovery and improve outcomes when applied for 24 to 72 hours in cases of traumatic brain injury. In particular, research suggests that brain damage from a stroke may take hours to reach maximum effect. Neurologic damage may be limited and the stroke victim's outcome improved if a neuroprotectant therapy, such as cooling, is applied within this time frame.

A TTM system using medical pads can regulate body temperature for patients who undergo procedures requiring therapeutic TTM and/or to assist in controlling temperature for specific medical or surgical conditions. Such a system is described in U.S. Pat. No. 6,645,232, titled "Patient Temperature Control System with Fluid Pressure Maintenance," and exemplary medical pads are described in U.S. Pat. No. 6,375,674, titled "Cooling/Heating Pad and System," each of which is incorporated by reference in its entirety into this application.

One problem that often arises with TTM systems is irritation of patients' skin due to pressure from an edge of the cooling and heating medical pads of the TTM system. Specifically, the medical pads may have a harsh edge, for example at curves or corners, that may cause discomfort and irritation for some patients. Even though the pads can contain a pliable material, like a hydrogel, that can conform to the patient's skin and provide good thermal contact, some patients may still experience skin irritation. In some cases, patients may use the pads for extended periods, exacerbating such discomfort and irritation after repeated contact. Embodiments of the disclosed apparatus and system can address this problem.

Reference is now made to FIG. 1, which illustrates a TTM system 100 using medical pads 120 for heating and/or cooling a patient P, according to some embodiments. The illustrated patient temperature control system 100 is a thermoregulatory system and apparatus that monitors and controls patient temperature within a range of 32° C. to 38.5° C. (89.6° F. to 101.3° F.). TTM system 100 is selectively interconnected to one or more medical contact pads 120 for exchanging thermal energy with patient P, and can also include a circulating pump for drawing temperature-controlled fluid (e.g., water or a gas) through pads 120 under negative pressure.

In some embodiments, TTM system 100 can include a control module 110, one or more disposable medical contact pads 120, a remote display in control module 110, a patient temperature probe 130, one or more fluid circulation lines 140, and any additional accessories. In a typical embodiment, there may be two pads 120 placed on the patient's upper body as shown, and two on the patient's lower body. The TTM system 100 uses negative pressure to draw temperature-controlled fluid, such as water ranging between 4° C. and 42° C. (39.2° F. and 107.6° F.), through the pads 120 at approximately 0.7 liters per minute per pad. This results in heat exchange between the circulating fluid and the patient P. The patient temperature probe 130 is connected to the control module 110, and provides patient temperature feedback information to an internal control algorithm of control module 110. Based on such an internal control algorithm, control module 110 can increase or decrease the circulating water temperature so as to heat or cool patient P to a target patient temperature, which can be set by the clinician.

Fluid circulation lines 140 may include opposing tubing assemblies for interconnection to outlet and inlet ports of the circulating pump, with pads 120 fluidly interconnectable by means of opposing pad manifolds. FIG. 1 also illustrates the interconnection of one or more external patient temperature sensors 130 with a signal conditioning interface of control module 110. The temperature information received from external temperature sensors 130 may be utilized at a processor of control module 110 to determine the amount and rate of thermal exchange to be affected by system 100 in relation to the preset or user-defined patient target temperature. Accordingly, the processor may provide appropriate control drive signals to a heater, radiator/fan and/or auxiliary pump of TTM system 100. In an embodiment, the circulating pump, heater, radiator/fan, and/or auxiliary pump may be housed within control module 110.

Figure 2:
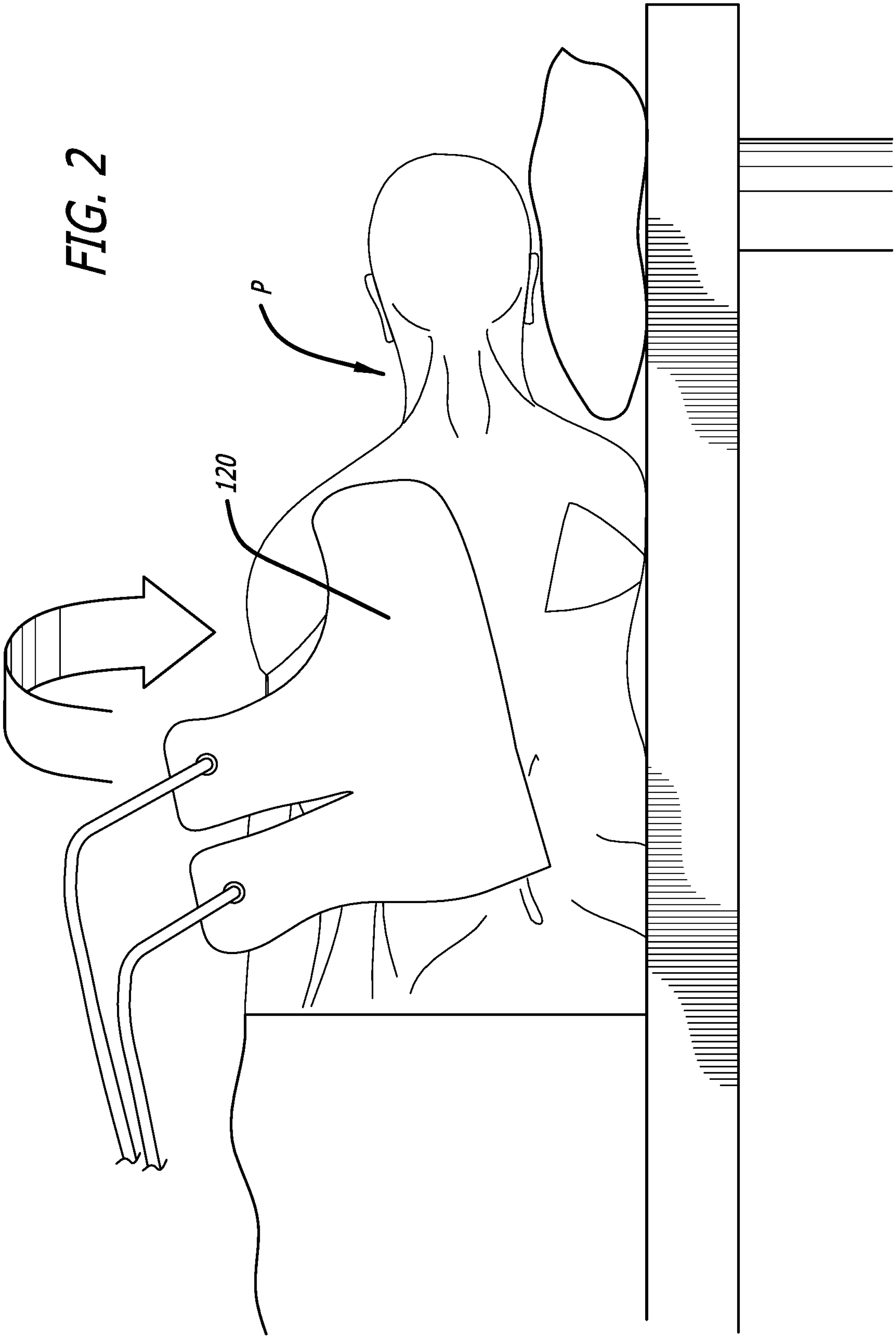
FIG. 2 illustrates TTM medical pads being placed on a patient, according to some embodiments.

FIG. 2 illustrates a TTM medical pad 120 being placed on a patient P, according to some embodiments. Pad 120, and particularly an inner layer of pad 120 containing biocompatible hydrogel, can conform to the patient's skin, and thereby provide good thermal contact with patient P. The medical pad 120 can include several layers: an inner biocompatible hydrogel layer that adheres and conforms to the patient P, a fluid containing layer, one or more thin film layers which serve as a fluid barrier, and an outer insulating layer which prevents heat transfer to the environment (see FIG. 3). The hydrogel layer can have sufficient adhesive strength to hold pads 120 in place on patient P during the TTM therapy, yet not cause tissue damage when subsequently removed.

The pads may be available in extra-small, small, medium, and large sizes, as well as a universal pad. The clinician can determine the style, size, and number of pads 120 to be applied to patient P based on the patient procedure, application, or the available body surface area on patient P. For example, the clinician may place two pads 120 on the patient's upper body, such as on the patient's back and torso as illustrated in FIG. 2, and two pads on the patient's lower body, for example wrapped around the patient's thighs. The medical pads 120 will provide the best performance when the maximum number and correct size are used.

Due to the negative fluid pressure applied by system 100, significant fluid leakage will not occur, even if pads 120 are damaged or broken while fluid is flowing. Accordingly, pads 120 can be applied to the patient while fluid is already flowing through the pads. Depending on the objective of the treatment and the patient's level of arousal, pads 120 may be pre-warmed or pre-cooled prior to placement.

In order to place TTM pad 120, a clinician will first align the top of a first upper body pad 120 with axilla of the patient's outstretched arm. The clinician will then place the long side of pad 120 along the side of the patient's spine. Next, the clinician can wrap pad 120 from back to front as illustrated, ensuring that the pad's fluid inlet and outlet lines are lying anteriorly. For the lower body, the clinician can align the first lower body pad's lines with the knee and point downward. The clinician will wrap the long end of the first lower body pad laterally, and overlap medially if needed.

The clinician may then turn the patient P and place a second upper body pad on the patient's other side, leaving a space along the patient's spine. Next, the clinician can wrap a second lower body pad around the patient's other leg, ensuring that the shorter edge is placed medially and the longer side is wrapped laterally. Finally, if additional surface coverage is needed, the clinician can optionally place a universal medical pad on the patient's abdomen.

The medical pads 120 have inlet and outlet lines for the fluid flow, referred to herein as pad lines. These lines are connected to the pads 120 by means of a pad manifold. In particular, a Y-shaped fluid delivery line contains one-way valves that connect to pad line connectors (e.g., a total of six connectors). Each side of the fluid delivery line can be placed by the patient's feet or along the patient's lower legs. The connectors can accommodate a full set of four pads 120 plus a maximum of two optional universal medical pads for larger patients. While holding the pad line tubing, the clinician can insert a pad line connector into the pad fluid delivery line manifold. For example, the clinician can push a respective connector toward the manifold to release associated catches, and then pull apart. Subsequently, the clinician can disconnect the lines, e.g., by squeezing wings on the connector together.

FIG. 3 illustrates a structure of an exemplary medical pad, according to some embodiments. TTM medical pad 120 comprises inner biocompatible hydrogel layer 340, which is a conformable, thermally conductive layer that can adjoin and conform to patient's skin 320. Further, the pad 120 may include an adhesive layer 341 disposed on the skin contacting side of the hydrogel layer 340 for adhering the pad 120 to the patient's skin 320. While not shown, a removable release liner may be provider over the adhesive surface 341 to protect the adhesive surface 341 from contamination while the pad 120 is not in use.

Pad 120 additionally comprises fluid containing layer 350 and insulation layer 360 for preventing loss of thermal energy to the environment. The fluid containing layer 350 can be defined between one or more film layers and/or insulation layer 360. The fluid can be heated or cooled to a temperature between 4° C. and 42° C. (39.2° F. and 107.6° F.), and can circulate through fluid containing layer 350, exchanging thermal energy 330 with patient's skin 320 via hydrogel layer 340, so as to warm or cool patient P to the target temperature. Although in this example, heat energy 330 is shown flowing from skin 320 to the fluid in layer 350, heat 330 can flow in either direction between patient P and layer 350, so as to heat or cool patient P to the target temperature.

Alternatively, in some embodiments, pad 120 comprises hydrogel layer 340, a thin film layer which serves as a fluid barrier, and outer insulating layer 360 comprising foam with water channels.

A hydrogel is an appropriate material for layer 340 because the hydrogel is biocompatible, its adhesive strength does not tend to increase over time as compared with traditional adhesive, it tends to envelop hair on patient's skin 320, thereby facilitating good thermal contact, and its high water content results in relatively high thermal conductivity.

Accordingly, hydrogel layer 340 may function as a thermally conductive layer, while also having sufficient adhesive properties so as to integrally provide an adhesive surface. Alternatively, in some embodiments, the conformable, thermally conductive layer and adhesive surface can be comprised of different materials. For example, an appropriate adhesive material may be sprayed or otherwise applied onto the surface of a layer of an appropriate conformable, thermally conductive material different than the adhesive material.

Fluid containing layer 350 can include tortuous fluid flow paths, which can be defined by dimples 361 or other elongated members on insulation layer 360 or within the fluid containing layer 350. Such tortuous fluid flow paths can serve to regulate the fluid flow, and to inhibit the formation of boundary layers wherein some of the fluid remains substantially stationary along the inside surfaces of the fluid containing layer 350. Such boundary layers could reduce the efficiency of the pad 120 because the stationary fluid remains within the fluid containing layer 350, but eventually becomes ineffective at heating or cooling patient P as it approaches the existing temperature of patient P. Furthermore, the crisscrossed geometry of elongated members defining the tortuous flow paths also facilitates an even, low pressure drop between the inlet and the outlet required by a negative flow pressure circulating system.

Even though medical pads 120 can contain a conformable, biocompatible material, like hydrogel layer 340, some patients may still experience skin irritation while using the pads 120. In some cases, discomfort and skin irritation may be caused by pressure from the edges of pads 120. Specifically, medical pads 120 may have a harsh or rough-textured edge, for example at corners or regions of curvature, that may cause discomfort and irritation for some patients. In some cases, patients may use the pads for extended periods, exacerbating such discomfort and irritation after repeated contact. The disclosed edge guard apparatus and system can address this problem.

FIG. 4 illustrates edge guards 410 and 420 surrounding the perimeter of a medical pad 120, according to some embodiments. The disclosed edge guards 410 and 420 may extend outwardly from the edge of pad 120, and surround some or all of the edge of pad 120. In order to reduce any irritation affecting the patient's skin 320 when in contact with TTM medical pad 120, edge guards 410 and 420 can be comprised of a soft or pliant material such as silicone, silicone polydimethylsiloxane (PDMS), silicone rubber, or siloxane, serving as a shock-absorbing barrier between pad 120 and skin 320. In some embodiments, another material may be used, such as low-density polyethylene (LDPE), ethylene-vinyl acetate (EVA), expanded polypropylene, polyether block amide (PEBA), polystyrene, an elastomer, another plastic, reinforced foam, latex, or rubber. Edge guards 410 and 420 can dissipate force from the pad 120 over wider areas (see FIG. 6A), and thereby ameliorate side effects resulting from TTM treatment, namely patient discomfort and skin irritation.

As described in the example of FIG. 3 above, the medical pad 120 comprises a hydrogel layer, which can contact and conform to the patient's skin, a film layer, which forms a base for fluid flow paths through pad 120, and an insulation layer, which prevents loss of thermal energy to the environment. Edge guards 410 and 420 can extend from the edges of pad 120, absorbing forces from the hydrogel layer and/or the other layers of pad 120. Because edge guards 410 and 420 are pliant, they may also conform to the patient's skin, as does pad 120.

In some embodiments, the disclosed edge guard may surround a portion of the perimeter. For example, the edge guard may be situated at a corner, bend, or curve, where the medical pad 120 may have a particularly harsh or rough-textured edge. In the example of FIG. 4, edge guards 410 and 420 are distinct, separate components, each covering a curve or corner of pad 120 (also see FIG. 6A). In particular, edge guard 410 is situated at a corner 430 of pad 120, which may be placed near a patient's axilla, as in the example of FIG. 2. Likewise, edge guard 420 is situated at a different corner 440 of pad 120, which may be placed near a patient's hip. Accordingly, edge guard 410 can protect the patient's axilla from irritation, while edge guard 420 can protect the patient's hip.

Alternatively, in some embodiments, the edge guard may surround substantially the entire perimeter of medical pad 120. FIG. 5 illustrates an edge guard 500 surrounding the perimeter 510 of a TTM medical pad 120, according to some embodiments. Thus, in the example of FIG. 5, a single edge guard 500 surrounds most or all of the edge 510 of pad 120, such that all edges 510 of pad 120 where pad 120 may rub or chafe against the patient's skin may be softened by edge guard 500 and made more comfortable for the patient. In another example, there may be multiple edge guards with only small gaps between them, thereby surrounding substantially the entire perimeter of pad 120. Alternatively, in some embodiments, the edge guard may have a different shape or size than those illustrated in FIGS. 4-6B, and is not limited by the present disclosure.

Compared with existing medical pads, the edge guard can reduce the pressure of pad edges on the patient's skin, thereby improving patient comfort and tolerance of the TTM treatment. A first way the edge guard improves comfort is by absorbing shock, for example by compressing and/or deforming in response to forces. In particular, the edge guard, which may comprise silicone or another pliant material, can be pliant enough to absorb or dissipate mechanical energy by elastically deforming. Second, the edge guard may also be soft, thereby cushioning the patient from pressure from the TTM pad. Likewise, the edge guard may have a smooth texture that makes comfortable contact with the patient's skin. Finally, the edge guard can reduce pressure on the patient's skin by transmitting forces from relatively sharp areas of the TTM pad to a broader surface area, as described in the example of FIG. 6A.

Figure 6A:
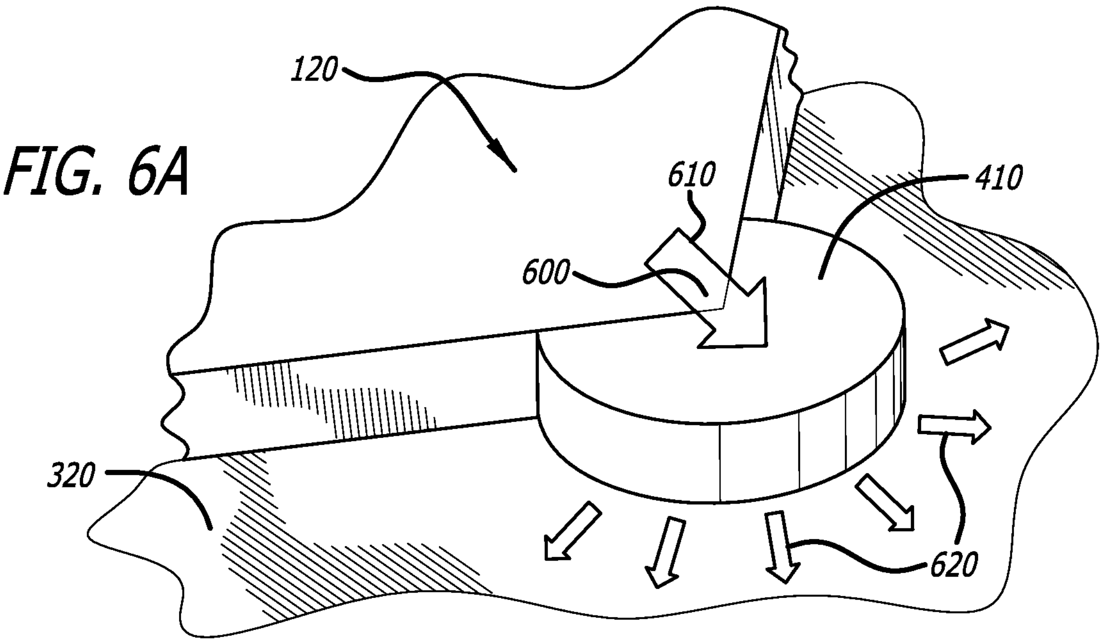
FIG. 6A illustrates a first embodiment of an edge guard distributing force from a portion of the edge of a medical pad, according to some embodiments.

FIG. 6A illustrates an edge guard 410 distributing force from a portion of the edge of a medical pad 120 (e.g., a corner portion 600), according to some embodiments. An operating principle of edge guard 410 is that it spreads forces applied to it across the broader, softer surface of the edge guard's border, and from the border to the patient's skin 320. By contrast, when pad 120 is placed on a patient without edge guard 410, especially large forces may accumulate at sharp segments of pad 120, such as corner 600. From these sharp segments, the large forces would be transmitted to the patient's skin 320.

In particular, the corner 600 may be sharp or harsh, and therefore, it may tend to irritate a patient during extended TTM treatment. Forces transmitted from the pad 120 will concentrate onto the small surface of the pad's corner 600, producing a high pressure, shown as a first force 610. However, as shown, edge guard 410 can have a significantly larger outer surface than corner 600, and accordingly the first force 610 can be distributed across a larger surface area, shown schematically as a plurality of second forces 620. Specifically, the plurality of second forces 620 is applied over a larger surfaced area of the patient's skin 320 and the sum thereof is equal to the first force 610.

By distributing the first force 610 across a larger surface area and improving patient comfort, edge guard 410 may provide the advantages of improved patient tolerance of the TTM treatment and lower likelihood of side effects, such as skin irritation or rashes. In this way, edge guard 410 can also contribute to further advantages, such as improved patient compliance with the treatment, and improved treatment efficacy. For example, a patient may be less likely to adjust his or her position, adjust the medical pad 120, or rub or scratch his or her skin 320, during the course of an extended TTM treatment when an edge guard 410 is utilized (e.g., due to a higher comfort level and less likelihood for the development of skin irritation). As a result, the treatment is more likely to be effective.

Edge guard 410 can provide these advantages when used jointly with medical pad 120, and indeed may be designed particularly for use with pad 120. For example, edge guard 410 may comprise a thermally conductive material, and thus may be designed to conduct heat between the fluid-containing hydrogel layer of pad 120 and the patient's skin 320. In further examples, edge guard 410 can have a rounded shape or a rounded wedge shape (see FIGS. 6B and 6C) designed to soften the sharp edges of the pad 120, or have a texture designed to be more comfortable than pad 120. Moreover, edge guard 410 may be designed to fit the shape and size of medical pad 120, for example by having a thickness that matches (or substantially matches) the total thickness of pad 120 or of the fluid containing layer, by having a curvature that matches a contour of the pad 120, or the like. In some embodiments, edge guard 410 can be designed to attach to the edge of medical pad 120 by an attachment mechanism, and/or by a more permanent bonding method, as described in the examples of FIGS. 7-9. In various embodiments, the rounded shape or rounded wedge shape of FIGS. 6B and 6C may be used together with an attachment mechanism, or may be used without the attachment mechanism (for example if used with a more permanent bonding method, such as adhesive).

Figure 6B:
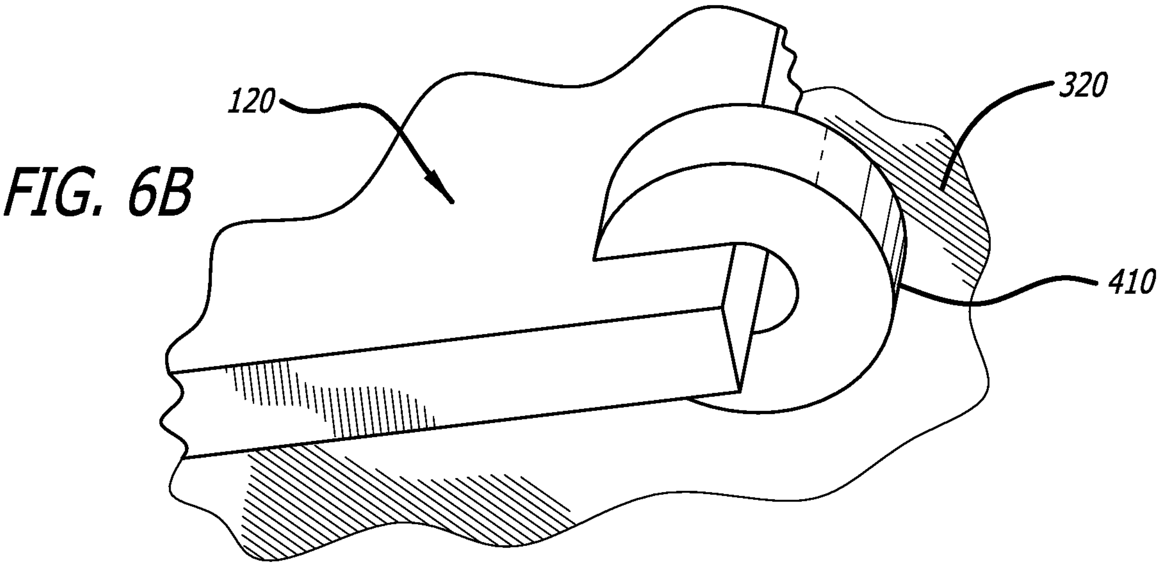
FIG. 6B illustrates a second embodiment of an edge guard distributing force from a portion of the edge of a medical pad, according to some embodiments.
Figure 6C:
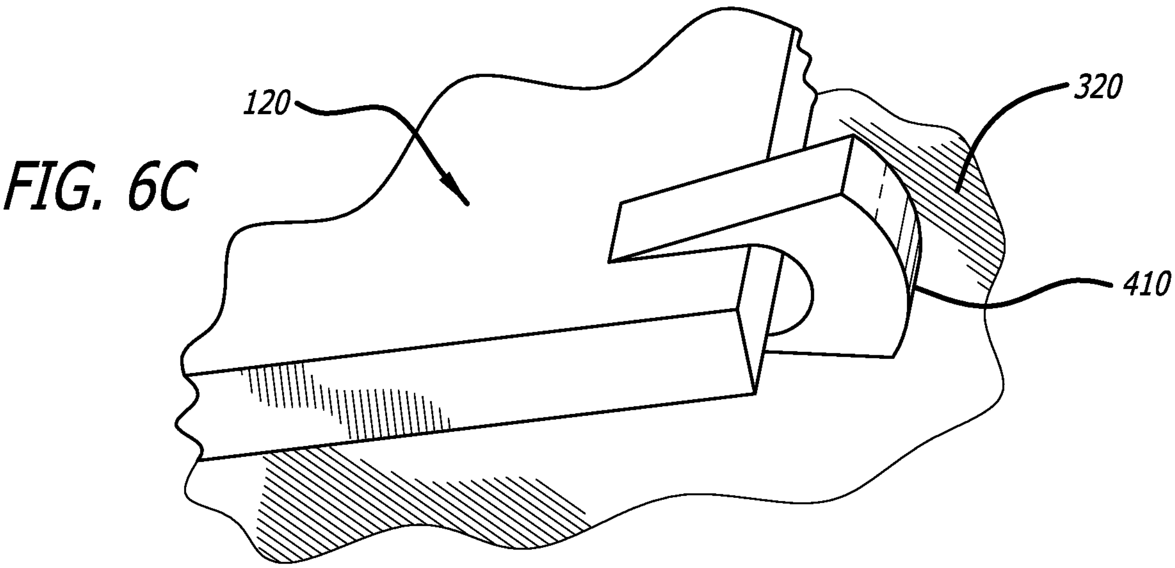
FIG. 6C illustrates a third embodiment of an edge guard distributing force from a portion of the edge of a medical pad, according to some embodiments.
Figure 6D:
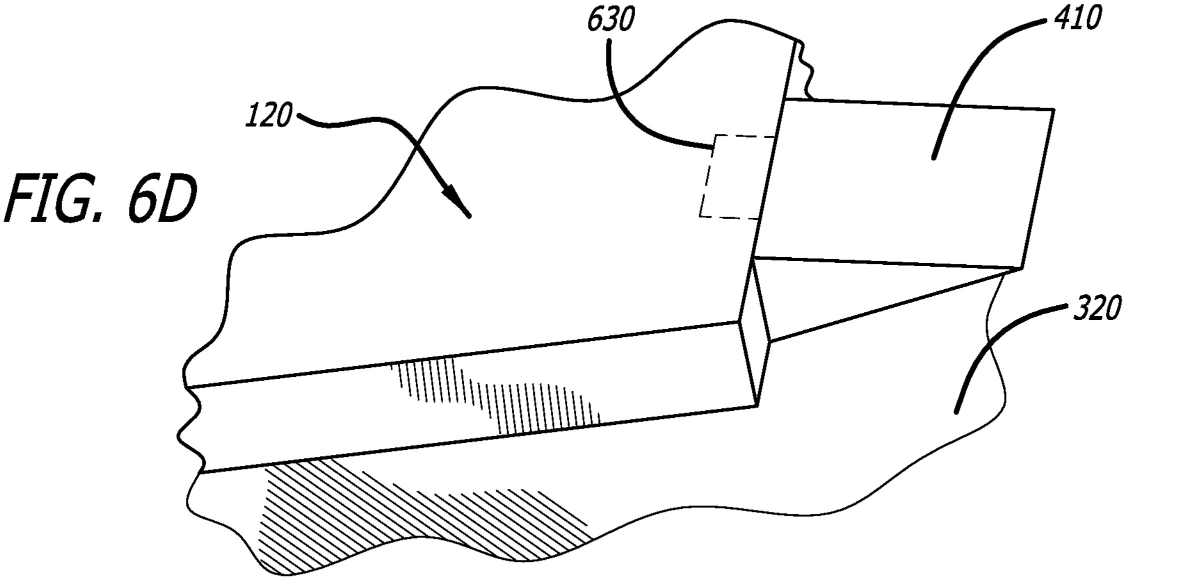
FIG. 6D illustrates a fourth embodiment of an edge guard distributing force from a portion of the edge of a medical pad, according to some embodiments.

Referring to FIG. 6D, an edge guard 410 having a tapered exterior edge is shown, according to some embodiments. Edge guard 410 may extend outwardly from the edge of pad 120, and be attached thereto, so as to serve as a flexible barrier between pad 120 and skin 320. In the example of FIG. 6D, edge guard 410 has a triangular solid shape, tapering from an initial thickness that covers the hydrogel layer, fluid containing layer, and insulation layer of pad 120.

Alternatively, edge guard 410 may have another shape or size, for example it may be shaped as a rectangular solid of thickness that covers all three layers of pad 120, a rectangular solid covering only the hydrogel layer, or a triangular solid tapering from an initial thickness of only the hydrogel layer. Furthermore, edge guard 410 may be formed in any other shape, such as a rectangular solid, rounded (see FIGS. 6A-6C), etc. In yet another embodiment, edge guard 410 may be pliant or flexible, such that the shape of edge guard 410 may conform to the patient's skin 320, and/or may deform in response to pressure, including for extended periods of time.

Because edge guard 410 may be pliant or flexible, it can absorb pressure or mechanical impacts from the edge of pad 120, as described in the example of FIG. 6A above, and cushion the patient's skin, thereby increasing patient comfort and improving patient tolerance, even during an extended TTM treatment. Moreover, edge guard 410 can function as a barrier between the edge of pad 120 and the patient's skin. That is, edge guard 410 can also prevent direct contact, rubbing, chafing, and the like between the edge of pad 120 and the patient's skin.

In some embodiments, edge guard 410 may contain a padded filling, such as soft foam, cotton gauze, or mesh, which can absorb pressure from the edges of medical pad 120, and thereby further taper and soften any harsh portions of pad 120. The attachment mechanism 630 represents any of the attachment mechanisms described herein, which may include those illustrated in FIGS. 7-9, as discussed below.

Figure 7:
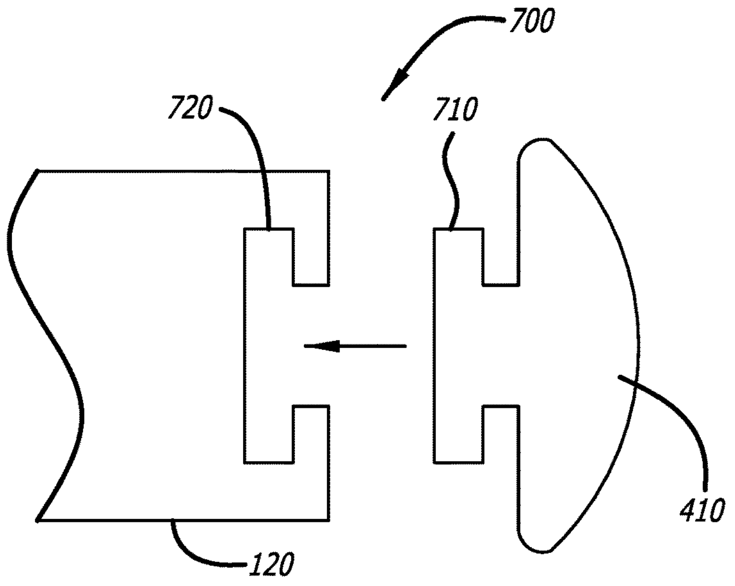
FIG. 7 illustrates an exemplary attachment mechanism of an edge guard to a medical pad, according to some embodiments.

FIG. 7 illustrates an exemplary attachment mechanism 700 of an edge guard 410 to a medical pad 120, according to some embodiments. In some embodiments, the edge guard 410 is locked on the edge of the pad 120 via a detachable attachment mechanism, also referred to herein as a channel-lock system. Applications of the pad to the patient (see FIG. 2) may involve high stress, rapid movements of the medical pad 120. Accordingly, the illustrated channel-lock system can prevent the edge guard 410 from moving or becoming dislodged during such rapid movements. In some embodiments, attachment mechanism 700 may be purposely detachable by a clinician, even while preventing inadvertent detachment of edge guard 410 during application or usage of pad 120.

In some embodiments, the attachment mechanism comprises a protruding member 710 on the interior of edge guard 410 interlocking with an indented recess 720 on the edge of pad 120. Because the shapes of the protruding member 710 and indented recess 720 are designed to fit together and interlock, the attachment mechanism is able to withstand significant pulling force without separating. In particular, edge guard 410 can remain attached to pad 120, even in the case of large pulling forces. Protruding member 710 and indented recess 720 may interlock in response to being mechanically pressed together, for example by a clinician while attaching edge guard 410 to pad 120.

In this example, protruding member 710 and indented recess 720 are shown as having piecewise linear outlines projected in the plane of FIG. 7. In various embodiments, protruding member 710 and indented recess 720 may have three-dimensional shapes, such as solids of revolution, or may be substantially flat. For example, protruding member 710 and indented recess 720 may be substantially flat or thin, that is they may extend out of the plane of FIG. 7 for only a small thickness, such as less than 5 cm, less than 1 cm, or less than 5 mm. Notwithstanding being thin, in another example, protruding member 710 and indented recess 720 may be shaped like solids of revolution. In this case, protruding member 710 may be disc-like, and indented recess 720 may be a cylindrical-shaped well. In still another example, protruding member 710 and indented recess 720 may be shaped like rectangular solids.

TTM pad 120 may be modified from its standard shape so as to include indented recess 720. Thus, in an embodiment, usage of edge guard 410 with a TTM pad 120 may require that the TTM pad 120 has been designed to interlock with it. In another embodiment, a standard TTM pad 120 can be retrofitted to interlock with edge guard 410, for example by adding a component that houses indented recess 720. In various embodiments, the attachment mechanism could be used with an edge guard having the rounded shape or rounded wedge shape of FIGS. 6B and 6C, or with any other shape of edge guard 410, and is not limited by the present disclosure.

Figure 8:
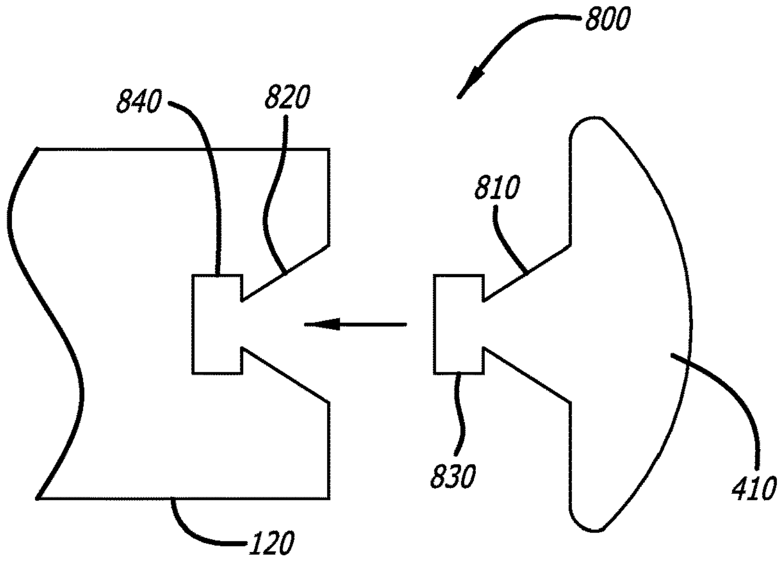
FIG. 8 illustrates another exemplary attachment mechanism of an edge guard to a medical pad.

FIG. 8 illustrates another exemplary attachment mechanism 800 comprising a convex member 810 on the interior of edge guard 410 interlocking with a concave well 820 on the edge of pad 120, according to some embodiments. In this example, the convex member 810 and the concave well 820 are largely conical in shape. Convex member 810 and concave well 820 can accordingly fit together easily and sturdily, for example when a clinical user mechanically presses them together.

In addition, convex member 810 has a protruding component 830, and concave well 820 has an indented recess 840, which is designed to fit together and interlock with protruding component 830. As a result, edge guard 410 can remain attached to pad 120 in spite of significant pulling forces, for example during high stress, rapid movements of the medical pad 120 such as may occur while applying pad 120 to the patient (see FIG. 2). Moreover, edge guard 410 can be purposely detached from pad 120 by a clinician. For example, the clinician can pull on the edge guard 410 so that protruding component 830 folds or deforms sufficiently to detach from indented recess 840, rotate the edge guard 410 or protruding component 830, or otherwise release attachment mechanism 800.

TTM pad 120 may be modified from its standard shape so as to include concave well 820. In another embodiment, a standard TTM pad 120 can be retrofitted to interlock with edge guard 410, for example by adding a component that houses concave well 820.

Figure 9:
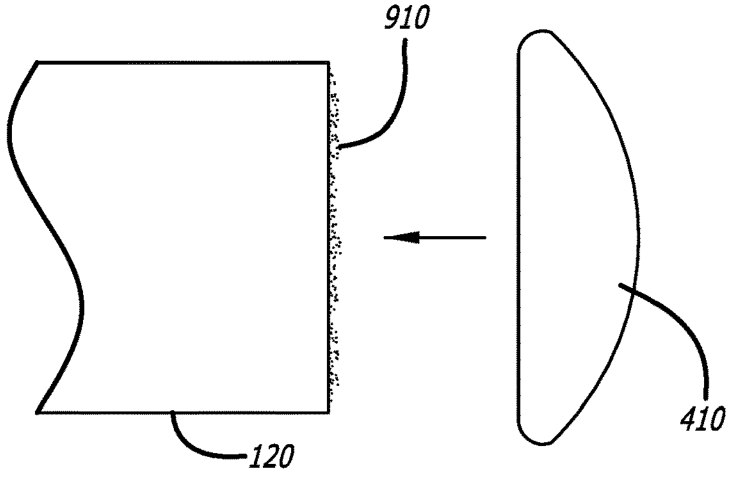
FIG. 9 illustrates an edge guard adhering to a medical pad, according to some embodiments.

FIG. 9 illustrates an edge guard 410 adhering to a medical pad 120, according to some embodiments. In some embodiments, the edge guard 410 may be semi-permanently or permanently attached to the pad 120, rather than detachably locked as in the examples of FIGS. 7-8 above. For example, a clinical user may not intend to detach edge guard 410 from TTM pad 120, but on the contrary may wish to eliminate any risk of inadvertent separation during the TTM procedure. Moreover, the user may prefer to eliminate any risk of clinical error, and to avoid expending any clinical time, associated with attaching edge guard 410 to pad 120 and/or operating an attachment mechanism. In such a case, the medical pad 120 may be distributed with one or more edge guards 410 permanently attached.

In this example, the edge guard 410 can be applied to pad 120 with an adhesive bond 910. As a result, there need not be any modification to the internal structure of medical pad 120. Rather, adhesive is added to the edge of pad 120. In this case, the edge guard 410 can be attached using adhesive bond 910 to either a standard medical pad 120, or a medical pad 120 designed to be used with edge guard 410. Consequently, the edge guard 410 may also be distributed separately from medical pad 120. In some embodiments, adhesive bond 910 may be antiseptic.

In some embodiments, adhesive 910 can be used in combination with an attachment mechanism (see FIGS. 7-8) to further strengthen the attachment. Alternatively, in some embodiments, edge guard 410 can be attached even more strongly to pad 120, for example using bolts or screws.

Figure 10A:
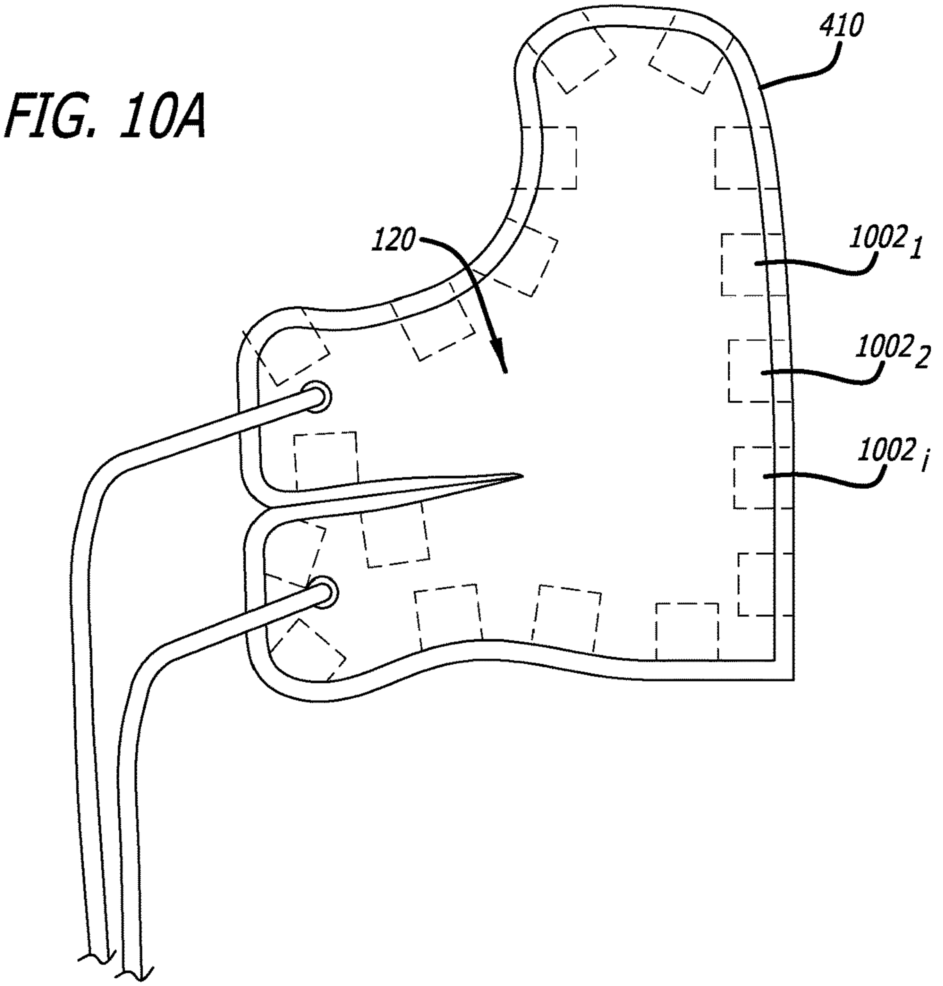
FIG. 10A illustrates an edge guard coupled with a medical pad including a plurality of attachment locations, according to some embodiments.

Referring now to FIG. 10A, an edge guard 410 attached to a gel pad 120 via any of the attachment mechanisms of FIGS. 7-9 at a plurality of attachment locations is shown. In some embodiments, the edge guard 410 may be specifically configured to conform to the size and shape of the pad 120 (e.g., the size of the edge guard 410 conforms to the outer circumference of the pad 120). In other embodiments the edge guard 410 may be individual strips of varying shapes (e.g., straight, having various angles, etc.) and varying sizes. Thus, the variations in the shapes and sizing of edge guards 410 may allow a clinician to attach one or more edge guards 410 to the pads 120 of varying shapes and sizes. Additionally, such variations allow a clinician to custom fit a pad 120 with edge guard(s) 410 as needed.

Figure 10B:
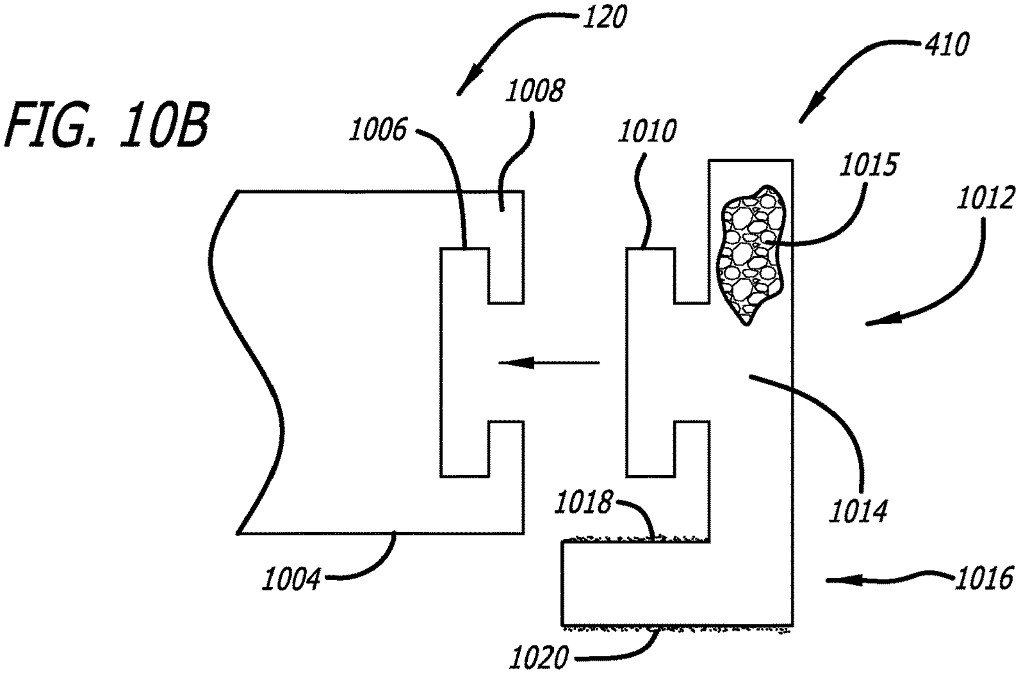
FIG. 10B illustrates an embodiment of an attachment location, according to some embodiments.

Referring now to FIG. 10B, an illustrative attachment location 1002$_1$ of a medical pad 120 and a corresponding edge guard 410 is shown, according to some embodiments. Specifically, an outer layer of the pad 120, e.g., the insulating layer 360 of FIG. 3, may be formed of a first material 1004. The attachment location 1002$_1$ of the pad 120 may be comprised of an outer edge including the indented recess area 1006 and formed from second material 1008 different than the first material 1004. For instance, the material 1008 may be silicone, vulcanized rubber, etc., thereby providing a firm attachment portion for interlocking with the edge guard 410.

In some embodiments, the edge guard 410 may be formed of multiple materials. For example, the portion of the edge guard 410 that interlocks with the pad 120, e.g., the protruding member 1010 on the interior of edge guard 410 (similar to FIG. 7) or the convex member 810 and the protruding component 830 of FIG. 8, may be formed of the second material 1008. Further, the cushioning portion 1012 of the edge guard 410 configured to absorb force from the edge of the pad 120 and distribute it across a greater surface area may be formed from a third material 1014.

In one example, the cushioning portion 1012 of the edge guard 410 forms an elastic outer shell. In some embodiments, the outer shell comprises a material such as, e.g., woven fabric, plastic (such as polyvinyl chloride (PVC), polyethylene, or polyurethane), or latex. In various embodiments, a portion of the outer shell may be adhesive, or a separate adhesive layer (e.g., adhesive layers 1018 and/or 1020) may cover a portion of outer shell, in order to adhere edge guard 400 to the patient's skin and/or to the pad 120.

Further, the edge guard 410 may contain a soft filling 1015, such as soft foam, cotton gauze, or mesh. In some embodiments, filling 1015 can comprise another material, such as polyester, wool, or latex. Filling 1015 can absorb pressure from the edges of medical pad 120, and can thereby soften the impact of medical pad 120, and particularly its harsh edges, on the patient's skin 320. Accordingly, medical pad 120 can remain on the patient's skin 320 during the course of extended TTM treatments, e.g., for hours or days, without irritating skin 320 or causing significant discomfort to the patient. In some embodiments, filling 1015 can include a thermally conductive material configured to conduct thermal energy between the pad 120 and the patient's skin 320. Additional detail and illustrations of the various fillings 1015 are described in U.S. Provisional Application No. 63/141,294, titled "Cooling/Heating Medical Pad with Softened Edges," which is incorporated by reference in its entirety into this application.

Additionally, FIG. 10B illustrates that the edge guard 410 may also include a portion 1016 that is disposed between the patient's skin and the pad 120, similar to the examples of FIGS. 6B-6C above. Additionally, the portion 1016 may include an internal adhesive layer 1018 configured to adhere the portion 1016 to the edge guard 120 and an external adhesive layer 1020 configured to adhere the portion 1016 to the patient's skin.

Figure 11A:
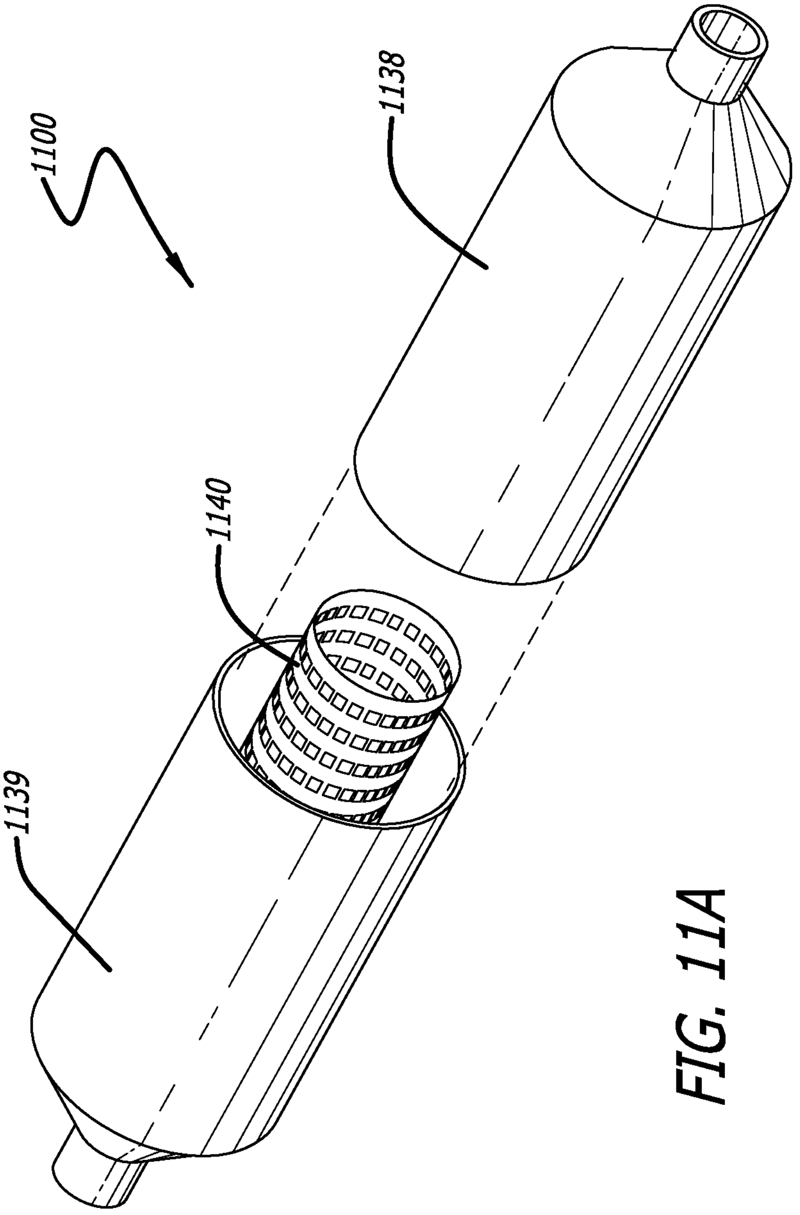
FIG. 11A provides an exploded perspective view of a TTM fluid filter, according to some embodiments.
Figure 11B:
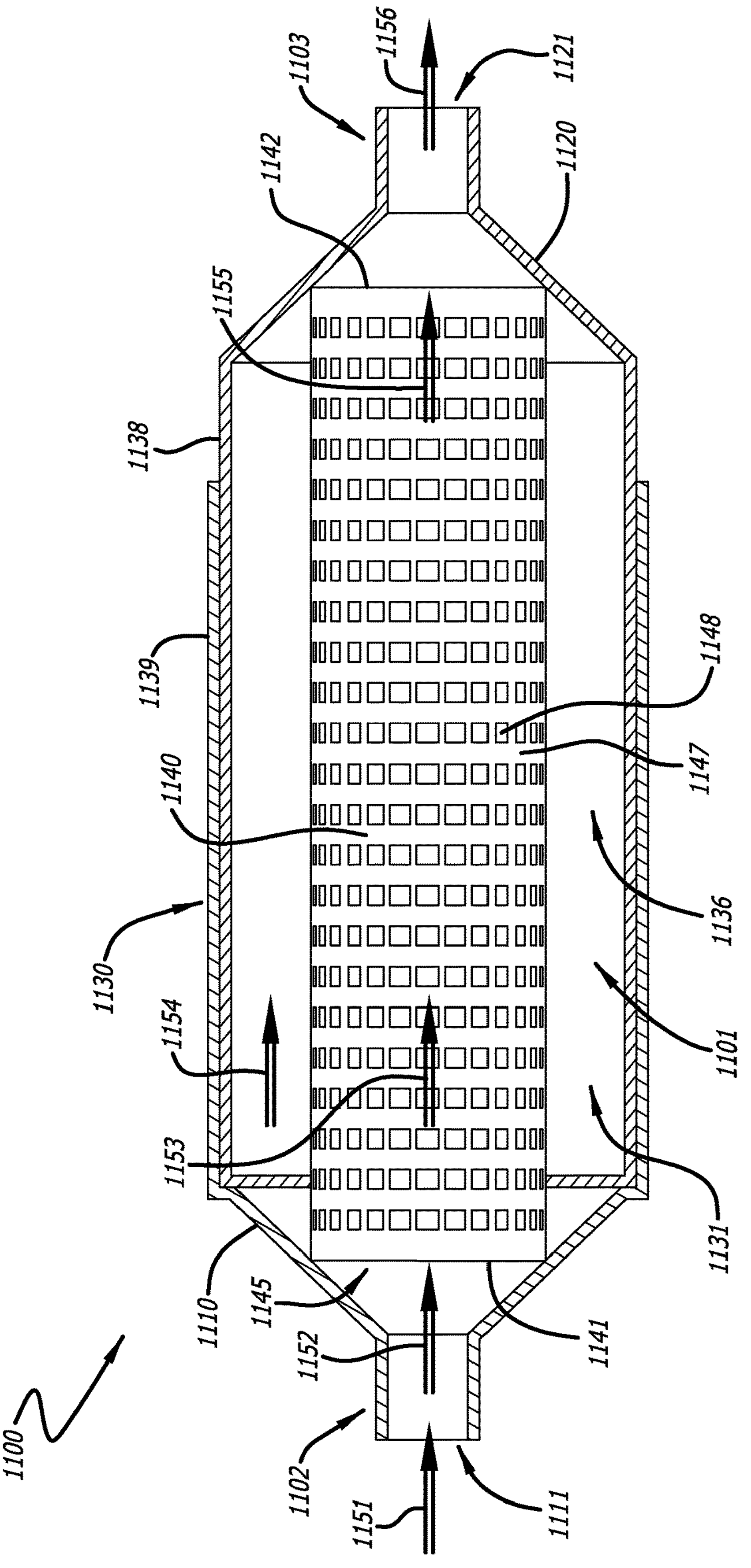
FIG. 11B provides a cross-sectional side view of the filter of FIG. 11A, according to some embodiments.

Referring now to FIGS. 11A-11B, a filter 1100 is illustrated that may be included with the TTM system 100, in accordance with some embodiments. The filter 1100 may be disposed in line with a TTM fluid flow path of the TTM system 100 so that the circulating TTM fluid flows through the filter 1100. The filter 1100 may be configured to remove (i.e., filter out) material/particles having a size of 0.2 microns or larger from the TTM fluid 112 without causing a flow restriction of the fluid 112.

The filter 1100 comprises a longitudinal shape having a flow path 1101 extending from a first end 1102 to a second end 1103. The filter 1100 comprises a diffuser 1110 adjacent the first end 1102, a nozzle adjacent 1120 the second end 1103, and a body 1130 extending between the diffuser 1110 and the nozzle 1120. Along the diffuser 1110, a cross-sectional flow area of the filter 1100 expands from an inlet flow area 1111 to a body flow area 1131 and along the nozzle 1120, the cross-sectional flow area of the filter 1100 contracts from the body flow area 1131 to an outlet flow area 1121. In some embodiments, the inlet flow area 1111 and the outlet flow area 1121 may be substantially equal.

In some embodiments, the body flow area 1131 may be constant along the body 1130. In other embodiments, the body flow area 1131 may vary along a length of the body 1130 such that the body flow area 1131 is greater or less along middle portion of the body 1130 than at the ends of the body 1130. In some embodiments, the body flow area 1131 may be circular.

The filter 1100 comprises an inner tube 1140 disposed within the body 1130 extending along the length of body 1130. The inner tube 1140 may be coupled to the diffuser 1110 at a first inner tube end 1141 so that fluid 112 entering the filter 1100 at the first end 1102 also enters the inner tube 1140 at the first inner tube end 1141. The inner tube 1140 may be coupled to the nozzle 1120 at a second inner tube end 1142 so that fluid 112 exiting the filter 1100 at the second end 1103 also exits the inner tube 1140 at the second inner tube end 1142.

The inner tube 1140 comprises an inner tube flow area 1145 extending the length of the inner tube 1140. The inner tube flow area 1145 may be greater than the inlet flow area 1111 and/or the outlet flow area 1121. The inner tube flow area 1145 may be constant along the length of the inner tube 1140. In some embodiments, the inner tube flow area 1145 may vary along the length of the inner tube 1140. In some embodiments, the inner tube 1140 may comprise a circular cross section. The inner tube 1140 and the body 1130 may be configured so that the body flow area 1131 comprises a combination of the inner tube flow area 1145 and an annular flow area 1136.

The inner tube 1140 comprises a porous a circumferential wall 1147. The porous wall 1147 may be configured so that fluid 112 may flow through the porous wall 1147, i.e., through the pores 1148 of the porous wall 1147. Consequently, fluid 112 may flow through the porous wall 1147 from the inner tube flow area 1145 to the annular flow area 1136 and from the annular flow area 1136 into the inner tube flow area 1145.

In use, the longitudinal velocity of the fluid 112 may change along the length of the filter 1100. As the volumetric fluid 112 flow through the filter is constant, the longitudinal velocity of the fluid 112 may be at least partially defined by the flow areas of the filter 1100 as described below. The fluid 112 may enter the filter 1100 at a first longitudinal velocity 1151 and decrease along the diffuser so that the fluid 112 enters the inner tube at a second velocity 1152 less than the first longitudinal velocity 1151. At this point, a portion of the fluid 112 may flow through the porous wall 1147 from the inner tube flow area 1145 into the annular flow area 1136 to divide the fluid flow into a third velocity 1153 within the inner tube flow area 1145 and a fourth velocity 1154 within the annular flow area 1136. The fourth velocity 1154 may be less than the third velocity 1153. A portion of the fluid 112 may then flow back into the inner tube flow area 1145 from the annular flow area 1136 to define a fifth velocity 1155 along the inner tube flow area 1145 which may be about equal to the second velocity 1152. The fluid 112 may then proceed along the nozzle 1120 to define a sixth velocity 1156 exiting the filter 1100. In some embodiments, the first velocity 1151 and the sixth velocity 1156 may be about equal.

The filter 1100 may be configured to remove harmful bacteria and viruses from the fluid 112 using sedimentation principles. In use, the filter 1100 may be oriented horizontally so that the direction of fluid flow through the filter 1100 is perpendicular to a gravitational force 1165. In some instances, bacteria, viruses, and other particles within the fluid 112 may have a greater density than the fluid 112 and as such may be urged by the gravitational force 1165 (i.e., sink) in a direction perpendicular to the fluid flow direction. In some instances, particles within the inner tube flow area 1145 may sink toward and through the porous wall 1147 into the annular flow area 1136. Particles within the annular flow area 1136 may then sink toward an inside surface 1131 of the body 1130 and become trapped adjacent the inside surface 1131. The geometry of the filter 1100 may be configured to allow 0.2-micron bacteria/virus particles to fall out of the flow of TTM fluid 112 and become trapped along the inside surface 1131.

In some embodiments, the filter 1100 may be configured so that flow of fluid 112 from the inner tube flow area 1145 into the annual flow area 1136 my drag particles through the porous wall 1147. In some embodiments, the inlet flow area 1111, the inner tube flow area 1145, and the annual flow area 1136 may be sized so that the third velocity 1153 is less than about 50 percent, 25 percent, or 10 percent of the first velocity 1151 or less. In some embodiments, the body 1130 and the inner tube 1140 may be configured so that the fourth velocity 1154 is less than the third velocity 1153. In some embodiments, the fourth velocity 1154 may less than about 50 percent, 25 percent, or 10 percent of the third velocity 1153 or less.

In some embodiments, the filter 1100 may be configured so that the flow within the inner tube flow area 1145 is laminar flow, i.e., so that the velocity of the fluid flow adjacent to or in close proximity to an inside surface 1141 of the porous wall 1147 is less than the velocity at a location spaced away from the inside surface 1141. In such an embodiment, the particles may more readily sink toward and through the porous wall 1147.

In some embodiments, the filter 1100 may be configured so that the fluid flow within the annual flow area 1136 is laminar flow, i.e., so that the velocity of the fluid flow adjacent to or in close proximity to inside surface 1131 of the body 1130 is less than the velocity at a location spaced away from the inside surface 1131. In such an embodiment, the particles may more readily sink toward and be trapped along the inside surface 1131.

The filter 1100 may comprise three components including the inner tube 1140 an inner body shell 1138, and an outer body shell 1139. Each of the three components may be formed via the plastic injection molding process. Assembly of the filter 1100 may include capturing the inner tube 1140 within the inner body shell 1138 and the outer body shell 1139 and sliding the inner body shell 1138 into the outer body shell 1139 wherein the fit between the inner body shell 1138 and the outer body shell 1139 is an interference fit.

Figure 11C:
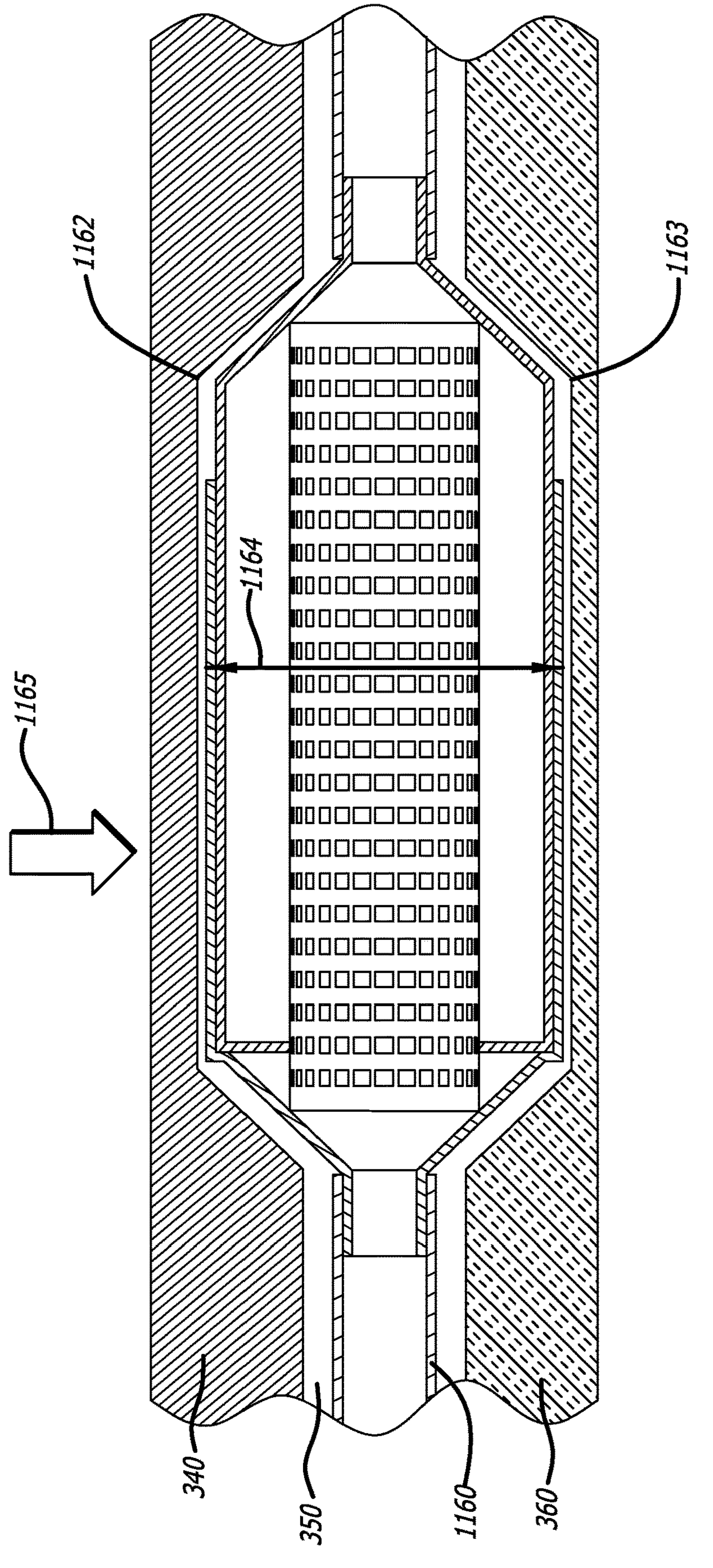
FIG. 11C provides a side cross-sectional view of the thermal contact pad of FIG. 1 incorporating the filter of FIG. 11A, according to some embodiments.

In some embodiments, the filter 1100 may be disposed within the pad 120. FIG. 11C shows a detail cross-sectional view of the pad 120 including the filter 1100 disposed within the fluid containing layer 350. The filter 1100 is coupled in line with an internal flow path 1160 within the fluid containing layer 350 so that fluid 112 circulating within the pad 120 passes through the filter 1100. The filter 1100 may be sized so that the inlet flow area 1111 and the outlet flow area 1121 are similar to a cross-sectional flow area of the internal flow path 1160 within the fluid containing layer 350. The internal flow path 1160 may be comprised of tubing (e.g., similar to the fluid delivery lines 140) that is disposed within the fluid containing layer 350. In such embodiments, the tubing of the internal flow path 1160 receives the fluid 112 from a fluid delivery line 140 at an inlet port. The fluid 112 flows through the tubing of the internal flow path 1160, passing through the filter 1100, toward an outlet port, at which point the fluid 112 exits the pad 120 and is received by a second fluid delivery line 140.

In some embodiments, a thickness of the fluid containing layer 350 may increase adjacent the filter 1100 to accommodate a body diameter 1164 of the filter 1100. To further accommodate the body diameter 1164, the insulation layer 360 and/or the thermal conduction layer 340 may comprise internal depressions 1162, 1163, respectively.

In some embodiments, one or more filters 1100 may be disposed in line with the flow of fluid 112 at other locations of the TTM system 100. In some embodiments, one or more filters 1100 may be disposed within the TTM module 110. In some embodiments, one or more filters 1100 may be disposed in line with one or more of the fluid delivery lines 140. In some embodiments, the filter 1100 may be disposed in line with a fluid conduit of the pad external to the fluid containing layer 350 such as a conduit extending between a pad connector and the pad 120.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical pad for exchanging thermal energy with a patient body, the medical pad comprising:

- a flexible upper sheet;
- a flexible base member interconnected to the flexible upper sheet to define a fluid containing layer between the flexible base member and the flexible upper sheet, wherein the fluid containing layer includes a plurality of tortuous fluid flow paths;
- an adhesive surface disposed on a skin-contacting side of the flexible upper sheet and adapted for releasable adhesive contact with skin of the patient body; and
- an edge guard comprising a pliant shock-absorbent material surrounding a portion of an edge of the flexible upper sheet, wherein:
  - the edge guard is configured to distribute pressure from the medical pad across a portion of the patient body in contact with a surface of the edge guard, and
  - the edge guard is locked on the portion of the edge of the flexible upper sheet via an attachment mechanism, the attachment mechanism comprising a convex member on an inside of the edge guard interlocking with a concave well on the portion of the edge of the flexible upper sheet.

2. The medical pad of claim 1, wherein the edge guard is configured to conduct thermal energy between the fluid containing layer and the patient body.

3. The medical pad of claim 1, wherein the pliant shock-absorbent material comprises silicone.

4. The medical pad of claim 1, wherein the edge guard is disposed on the portion of the edge of the flexible upper sheet via an adhesive bond.

5. The medical pad of claim 1, wherein the convex member and the concave well are conical.

6. The medical pad of claim 1, wherein the portion of the edge comprises at least a corner of the edge of the flexible upper sheet.

7. The medical pad of claim 1, further comprising a conformable, thermally conductive layer of a hydrogel material.

8. The medical pad of claim 1, wherein the flexible base member includes a plurality of dimples defining the plurality of tortuous fluid flow paths.

9. The medical pad of claim 8, wherein the plurality of dimples are of a predetermined configuration comprising one or more of:

- a truncated cone configuration,
- a cylindrical configuration, and
- an elongated, truncated pyramid configuration.

10. The medical pad of claim 8, wherein:

- the plurality of dimples are arranged in a predetermined staggered pattern on an upper surface of the flexible base member,
- a lower smooth surface of the flexible upper sheet is supported at a plurality of points of contact with the plurality of dimples, and
- the plurality of dimples are staggered in at least two transverse directions on the upper surface of the flexible base member.

11. The medical pad of claim 10, wherein the predetermined staggered pattern comprises offset rows and columns.

12. The medical pad of claim 11, wherein the plurality of dimples within adjacent rows and adjacent columns are offset from one another by sixty degrees.

13. The medical pad of claim 10, wherein the plurality of dimples are arranged in a herringbone pattern.

14. The medical pad of claim 10, wherein the flexible base member is formed to integrally define the plurality of dimples.

15. The medical pad of claim 1, further comprising a filter disposed in line with a fluid flow path providing a fluid to the medical pad.

16. The medical pad of claim 15, wherein the filter comprises a porous wall disposed parallel to a flow direction of the fluid along the fluid flow path.

17. The medical pad of claim 15, wherein the filter is attached to the medical pad.

18. The medical pad of claim 15, wherein the filter is disposed within the fluid containing layer of the medical pad.

19. A medical pad for exchanging thermal energy with a patient body, the medical pad comprising:

- a flexible base member of foam construction having a plurality of integrally defined dimples;
- a flexible film interconnected to the flexible base member to define a fluid containing layer between the flexible base member and the flexible film, wherein the plurality of integrally defined dimples define tortuous fluid flow paths within the fluid containing layer;
- a thermally conductive layer laminated to one side of the flexible film;

an adhesive surface disposed on the thermally conductive layer and adapted for releasable adhesive contact with skin of a patient; and an edge guard comprising a pliant shock-absorbent material surrounding a portion of an edge of the thermally conductive layer, wherein:

the edge guard is configured to distribute pressure from the medical pad across a portion of the patient body in contact with a surface of the edge guard, and the edge guard is locked on the portion of the edge of the thermally conductive layer via an attachment mechanism, the attachment mechanism comprising a convex member on an inside of the edge guard interlocking with a concave well on the portion of the edge of the thermally conductive layer.

20. The medical pad of claim 19, wherein the edge guard is configured to conduct thermal energy between the fluid containing layer and the patient.

21. The medical pad of claim 19, wherein the pliant shock-absorbent material comprises silicone.

22. The medical pad of claim 19, wherein the edge guard is disposed on the portion of the edge of the thermally conductive layer via an adhesive bond.

23. The medical pad of claim 19, wherein the convex member and the concave well are conical.

24. The medical pad of claim 19, wherein the portion of the edge comprises at least a corner of the edge of the thermally conductive layer.

25. The medical pad of claim 19, wherein the thermally conductive layer comprises a conformable hydrogel material.

26. The medical pad of claim 19, wherein the plurality of integrally defined dimples defining the tortuous fluid flow paths are of a predetermined configuration comprising one or more of:

a truncated cone configuration, a cylindrical configuration, and an elongated, truncated pyramid configuration.

27. The medical pad of claim 19, further comprising a filter disposed in line with a fluid flow path providing a fluid to the medical pad.

28. The medical pad of claim 27, wherein the filter comprises a porous wall disposed parallel to a flow direction of the fluid along the fluid flow path.

29. The medical pad of claim 27, wherein the filter is attached to the medical pad.

30. The medical pad of claim 27, wherein the filter is disposed within the fluid containing layer of the medical pad.

* * * * *